(12) United States Patent
Ebner et al.

(10) Patent No.: US 12,672,828 B2
(45) Date of Patent: Jul. 7, 2026

(54) HIGH DENSITY PADDLE CATHETER WITH DISTAL COUPLER AND DISTAL ELECTRODE

(71) Applicant: St. Jude Medical, Cardiology Division, Inc., St. Paul, MN (US)

(72) Inventors: Bruce Ebner, Shorewood, MN (US); Hong Cao, Maple Grove, MN (US); Vlad Popov, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 355 days.

(21) Appl. No.: 18/476,091

(22) Filed: Sep. 27, 2023

(65) Prior Publication Data

US 2024/0099660 A1    Mar. 28, 2024

Related U.S. Application Data

(60) Provisional application No. 63/435,886, filed on Dec. 29, 2022, provisional application No. 63/410,758, filed on Sep. 28, 2022.

(51) Int. Cl.
*A61B 5/00* (2006.01)
*A61B 5/287* (2021.01)
(Continued)

(52) U.S. Cl.
CPC ............ *A61B 5/6859* (2013.01); *A61B 5/287* (2021.01); *A61B 5/367* (2021.01);
(Continued)

(58) Field of Classification Search
CPC ... A61B 5/287; A61B 5/6859; A61B 18/1492; A61B 2018/0016; A61B 2018/00178;
(Continued)

(56) References Cited

U.S. PATENT DOCUMENTS

| | | | |
|---|---|---|---|
| 4,522,212 A | 6/1985 | Gelinas et al. |
| 5,224,939 A | 7/1993 | Holman et al. |

(Continued)

FOREIGN PATENT DOCUMENTS

| | | |
|---|---|---|
| AU | 2015202258 A1 | 5/2015 |
| AU | 2016204351 A1 | 1/2017 |

(Continued)

*Primary Examiner* — Eun Hwa Kim
(74) *Attorney, Agent, or Firm* — Kilpatrick Townsend & Stockton LLP

(57) ABSTRACT

A catheter (e.g., high-density mapping catheter) and related catheter system is described herein. The catheter includes an elongated catheter shaft, and an electrode assembly. The electrode assembly includes a first spline assembly, a second spline assembly, and a distal coupler assembly. Each of the spline assembly includes a distal portion and spline assembly electrodes distributed along the spline assembly. The distal coupler assembly includes a base member and a distal electrode. The base member defines an opening configured to receive and accommodate the distal portion of the second spline assembly. The distal electrode is configured to be mounted to the base member to secure the distal portion of the second spline assembly within the opening. The distal electrode can be configured for cardiac mapping, tissue ablation, and/or bipolar pacing.

25 Claims, 11 Drawing Sheets

(51) Int. Cl.

| | |
|---|---|
| *A61B 5/367* | (2021.01) |
| *A61B 18/14* | (2006.01) |
| *A61N 1/362* | (2006.01) |
| *A61B 18/00* | (2006.01) |

(52) U.S. Cl.
CPC ........ *A61B 18/1492* (2013.01); *A61N 1/3621*
(2013.01); *A61B 2018/0016* (2013.01); *A61B*
*2018/00178* (2013.01); *A61B 2018/00351*
(2013.01); *A61B 2018/00577* (2013.01); *A61B*
*2018/00839* (2013.01); *A61B 2562/0257*
(2013.01); *A61B 2562/043* (2013.01); *A61B*
*2562/227* (2013.01)

(58) Field of Classification Search
CPC ........... A61B 2018/00351; A61B 2018/00839;
A61B 2018/00172; A61B 2018/00267;
A61B 2018/0212; A61B 2018/1467;
A61B 2018/1495
See application file for complete search history.

(56) References Cited

U.S. PATENT DOCUMENTS

| | | | |
|---|---|---|---|
| 5,380,301 A | 1/1995 | Prichard et al. |
| 5,400,783 A | 3/1995 | Pomeranz et al. |
| 5,456,254 A | 10/1995 | Pietroski et al. |
| 5,626,136 A | 5/1997 | Webster, Jr. |
| 5,702,438 A | 12/1997 | Avitall |
| 5,715,817 A | 2/1998 | Stevens-Wright et al. |
| 5,715,832 A | 2/1998 | Koblish et al. |
| 5,827,278 A | 10/1998 | Webster, Jr. |
| 5,876,373 A | 3/1999 | Giba et al. |
| 5,964,757 A | 10/1999 | Ponzi |
| 6,029,091 A | 2/2000 | de la Rama et al. |
| 6,071,282 A | 6/2000 | Fleischman |
| 6,074,379 A | 6/2000 | Prichard |
| 6,123,699 A | 9/2000 | Webster, Jr. |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 6,273,404 B1 | 8/2001 | Holman et al. |
| 6,415,187 B1 | 7/2002 | Kuzma et al. |
| 6,491,681 B1 | 12/2002 | Kunis et al. |
| 6,522,932 B1 | 2/2003 | Kuzma et al. |
| 6,554,794 B1 | 4/2003 | Mueller et al. |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,004,937 B2 | 2/2006 | Lentz et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,214,220 B2 | 5/2007 | McGlinch et al. |
| 7,217,256 B2 | 5/2007 | Di Palma |
| 7,228,164 B2 | 6/2007 | Fuimaono et al. |
| 7,257,435 B2 | 8/2007 | Plaza |
| 7,263,397 B2 | 8/2007 | Hauck et al. |
| 7,412,274 B2 | 8/2008 | Mejia |
| 7,429,261 B2 | 9/2008 | Kunis et al. |
| 7,561,907 B2 | 7/2009 | Fuimaono et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,885,707 B2 | 2/2011 | Hauck |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,157,848 B2 | 4/2012 | Zhang et al. |
| 8,221,390 B2 | 7/2012 | Pal et al. |
| 8,271,099 B1 | 9/2012 | Swanson |
| 8,273,016 B2 | 9/2012 | O'Sullivan |
| 8,376,990 B2 | 2/2013 | Ponzi et al. |
| 8,391,947 B2 | 3/2013 | Urman et al. |
| 8,447,377 B2 | 5/2013 | Harlev et al. |
| 8,486,063 B2 | 7/2013 | Werneth et al. |
| 8,565,894 B2 | 10/2013 | Vetter et al. |
| 8,603,069 B2 | 12/2013 | Selkee |
| 8,608,703 B2 | 12/2013 | Riles et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,744,599 B2 | 6/2014 | Tegg |
| 8,755,861 B2 | 6/2014 | Harlev et al. |
| 8,771,267 B2 | 7/2014 | Kunis et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,979,841 B2 | 3/2015 | Kunis et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,044,245 B2 | 6/2015 | Condie et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,474,486 B2 | 10/2016 | Eliason et al. |
| 9,486,280 B2 | 11/2016 | Koblish et al. |
| 9,486,282 B2 | 11/2016 | Solis |
| 9,522,035 B2 | 12/2016 | Highsmith |
| 9,532,703 B2 | 1/2017 | Huszar et al. |
| 9,539,413 B2 | 1/2017 | Ogle |
| 9,629,675 B2 | 4/2017 | Kleshinski et al. |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,694,159 B2 | 7/2017 | Schneider et al. |
| 9,694,161 B2 | 7/2017 | Selkee |
| 9,713,418 B2 | 7/2017 | Huszar et al. |
| 9,788,895 B2 | 10/2017 | Solis |
| 9,820,664 B2 | 11/2017 | Hoitink et al. |
| 9,833,608 B2 | 12/2017 | Masson |
| 9,844,645 B2 | 12/2017 | Pai et al. |
| 9,848,795 B2 | 12/2017 | Marecki et al. |
| 9,907,480 B2 | 3/2018 | Basu et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,069,668 B2 | 9/2018 | Cohen et al. |
| 10,099,036 B2 | 10/2018 | Heideman et al. |
| 10,118,022 B2 | 11/2018 | Helgeson et al. |
| 10,130,423 B1 | 11/2018 | Viswanathan et al. |
| 10,136,829 B2 | 11/2018 | Deno et al. |
| 10,143,394 B2 | 12/2018 | Solis |
| 10,172,673 B2 | 1/2019 | Viswanathan et al. |
| 10,285,610 B2 | 5/2019 | Wu |
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,470,682 B2 | 11/2019 | Deno et al. |
| 10,478,247 B2 | 11/2019 | Litscher et al. |
| 10,478,325 B2 | 11/2019 | Syed |
| 10,492,729 B2 | 12/2019 | de la Rama et al. |
| 10,506,938 B2 | 12/2019 | Wu et al. |

(56)　　　　　　References Cited

U.S. PATENT DOCUMENTS

| | | | |
|---|---|---|---|
| 10,537,259 | B2 | 1/2020 | Wu et al. |
| 10,542,899 | B2 | 1/2020 | Wu et al. |
| 10,556,091 | B2 | 2/2020 | Truhler et al. |
| 10,575,742 | B2 | 3/2020 | Wu et al. |
| 10,575,745 | B2 | 3/2020 | Solis |
| 10,578,737 | B2 | 3/2020 | Gliner et al. |
| 10,595,738 | B2 | 3/2020 | Sterrett et al. |
| 10,595,740 | B2 | 3/2020 | Hoitink et al. |
| 10,602,948 | B2 | 3/2020 | Wu et al. |
| 10,646,692 | B2 | 5/2020 | Tegg et al. |
| 10,653,423 | B2 | 5/2020 | Starnes |
| 10,702,177 | B2 | 7/2020 | Aujla |
| 10,702,677 | B2 | 7/2020 | Okamura et al. |
| 10,737,060 | B2 | 8/2020 | Gupta et al. |
| 10,813,590 | B2 | 10/2020 | Ruppersberg |
| 10,835,712 | B2 | 11/2020 | Wada |
| 10,842,990 | B2 | 11/2020 | de la Rama et al. |
| 10,857,349 | B2 | 12/2020 | de la Rama et al. |
| 10,869,992 | B2 | 12/2020 | Pai et al. |
| 10,898,685 | B2 | 1/2021 | Tegg |
| 10,905,347 | B2 | 2/2021 | Fuentes-Ortega et al. |
| 10,912,925 | B2 | 2/2021 | Houck |
| 10,932,685 | B2 | 3/2021 | Wu |
| 10,945,626 | B2 | 3/2021 | Fuentes-Ortega et al. |
| 10,946,167 | B2 | 3/2021 | Mintz et al. |
| 10,953,196 | B2 | 3/2021 | Raab et al. |
| 10,959,636 | B2 | 3/2021 | Dahlen et al. |
| 10,966,623 | B2 | 4/2021 | Wu et al. |
| 10,966,753 | B2 | 4/2021 | Coyle et al. |
| 10,967,150 | B2 | 4/2021 | Helgeson et al. |
| 10,973,427 | B2 | 4/2021 | Aujla |
| 10,987,045 | B2 | 4/2021 | Basu et al. |
| 11,033,715 | B2 | 6/2021 | Beeckler et al. |
| 11,039,772 | B2 | 6/2021 | Wu et al. |
| 11,039,773 | B2 | 6/2021 | Sterrett et al. |
| 11,077,298 | B2 | 8/2021 | Waldhauser et al. |
| 11,083,400 | B2 | 8/2021 | Hoitink et al. |
| 11,116,436 | B2 | 9/2021 | Wu et al. |
| 11,116,476 | B2 | 9/2021 | Buesseler et al. |
| 11,116,942 | B2 | 9/2021 | Beeckler et al. |
| 11,123,051 | B2 | 9/2021 | Van Der Linde et al. |
| 11,141,568 | B2 | 10/2021 | Hsueh et al. |
| 11,160,482 | B2 | 11/2021 | Solis |
| 11,172,858 | B2 | 11/2021 | Olson et al. |
| D940,310 | S | 1/2022 | de la Rama et al. |
| 11,272,886 | B2 | 3/2022 | Harlev et al. |
| D951,438 | S | 5/2022 | de la Rama et al. |
| D952,140 | S | 5/2022 | de la Rama et al. |
| D952,843 | S | 5/2022 | de la Rama et al. |
| 11,382,690 | B2 | 7/2022 | Smith et al. |
| 11,382,743 | B2 | 7/2022 | Marchand et al. |
| 11,383,078 | B2 | 7/2022 | De La Rama et al. |
| 11,419,673 | B2 | 8/2022 | Kauphusman et al. |
| 11,426,111 | B2 | 8/2022 | Olson |
| 11,433,220 | B2 | 9/2022 | Oliverius et al. |
| 11,439,460 | B2 | 9/2022 | Sliwa et al. |
| 11,446,470 | B2 | 9/2022 | Castelli et al. |
| 11,446,471 | B2 | 9/2022 | Grunewald |
| D966,506 | S | 10/2022 | de la Rama et al. |
| D966,507 | S | 10/2022 | de la Rama et al. |
| 11,478,299 | B2 | 10/2022 | Webster et al. |
| 11,484,690 | B2 | 11/2022 | Tegg et al. |
| 11,491,311 | B2 | 11/2022 | Selkee |
| 11,504,205 | B2 | 11/2022 | Brucker et al. |
| 11,511,078 | B2 | 11/2022 | Gonzalez |
| 11,517,715 | B2 | 12/2022 | Govari |
| 11,517,716 | B2 | 12/2022 | Nguyen et al. |
| 11,523,748 | B2 | 12/2022 | Esguerra Wilczynski et al. |
| 11,540,876 | B2 | 1/2023 | Oliverius et al. |
| 11,540,878 | B2 | 1/2023 | Fuentes-Ortega et al. |
| 11,547,437 | B2 | 1/2023 | Zarembinski |
| 11,553,962 | B2 | 1/2023 | Harlev et al. |
| 11,559,663 | B2 | 1/2023 | Hannon et al. |
| 11,583,334 | B2 | 2/2023 | Caples et al. |
| 11,583,658 | B2 | 2/2023 | Yang et al. |
| 11,602,630 | B2 | 3/2023 | Vetter et al. |
| 11,617,616 | B2 | 4/2023 | Clark et al. |
| 11,617,859 | B2 | 4/2023 | Hsueh et al. |
| 11,617,861 | B2 | 4/2023 | Pai et al. |
| 11,622,806 | B2 | 4/2023 | Romoscanu |
| 11,628,009 | B2 | 4/2023 | Aujla |
| 11,660,119 | B2 | 5/2023 | Hassett |
| 11,672,947 | B2 | 6/2023 | Tegg et al. |
| 11,684,473 | B2 | 6/2023 | Righini et al. |
| 11,690,552 | B2 | 7/2023 | Wu et al. |
| 11,723,574 | B2 | 8/2023 | Wu et al. |
| 11,771,373 | B2 | 10/2023 | Nakar et al. |
| 11,779,770 | B2 | 10/2023 | Botzer |
| 11,786,301 | B2 | 10/2023 | Olson |
| 11,806,152 | B2 | 11/2023 | Zeidan et al. |
| 11,813,410 | B2 | 11/2023 | Olson et al. |
| 11,832,965 | B2 | 12/2023 | Wang |
| 11,850,051 | B2 | 12/2023 | Selkee et al. |
| 11,857,250 | B2 | 1/2024 | Corvi et al. |
| 11,896,819 | B2 | 2/2024 | Rosa et al. |
| 11,904,109 | B2 | 2/2024 | Gliner et al. |
| 11,938,316 | B2 | 3/2024 | Feler et al. |
| 11,950,827 | B2 | 4/2024 | Rafiee et al. |
| 11,950,840 | B2 | 4/2024 | Govari et al. |
| 11,950,841 | B2 | 4/2024 | Govari et al. |
| 11,950,897 | B2 | 4/2024 | Esguerra Wilczynski et al. |
| 11,950,930 | B2 | 4/2024 | Gliner et al. |
| 11,957,847 | B2 | 4/2024 | Houck |
| 11,992,321 | B2 | 5/2024 | Solis |
| 12,004,804 | B2 | 6/2024 | Govari et al. |
| 12,004,805 | B2 | 6/2024 | Schuler et al. |
| 12,011,216 | B2 | 6/2024 | Zirkle et al. |
| 12,036,027 | B2 | 7/2024 | Olson et al. |
| 12,036,371 | B2 | 7/2024 | Hsueh et al. |
| 12,064,168 | B2 | 8/2024 | Harlev et al. |
| 12,076,079 | B2 | 9/2024 | Oliverius et al. |
| 12,083,288 | B2 | 9/2024 | Lopez et al. |
| 12,089,940 | B2 | 9/2024 | Hoitink et al. |
| 12,097,034 | B2 | 9/2024 | Wu et al. |
| 12,102,382 | B2 | 10/2024 | Govari et al. |
| 12,109,031 | B2 | 10/2024 | Deno et al. |
| 12,109,373 | B2 | 10/2024 | Srivastava et al. |
| 12,114,922 | B2 | 10/2024 | Harlev et al. |
| 12,121,357 | B2 | 10/2024 | de la Rama et al. |
| 12,121,438 | B2 | 10/2024 | Dehdashtian et al. |
| 12,138,404 | B2 | 11/2024 | Beeckler et al. |
| 12,144,629 | B2 | 11/2024 | Wu et al. |
| 12,171,488 | B2 | 12/2024 | Narayan et al. |
| 12,178,500 | B2 | 12/2024 | Highsmith |
| 12,185,961 | B2 | 1/2025 | Nguyen et al. |
| 12,186,010 | B2 | 1/2025 | Govari et al. |
| 12,193,728 | B2 | 1/2025 | Narayan |
| 12,193,823 | B2 | 1/2025 | Wu et al. |
| 12,194,251 | B2 | 1/2025 | Tavallaei et al. |
| 12,201,351 | B2 | 1/2025 | Kim et al. |
| 12,201,421 | B2 | 1/2025 | Garai et al. |
| 12,207,795 | B2 | 1/2025 | Purohit et al. |
| 12,214,206 | B2 | 2/2025 | Ward et al. |
| 12,220,541 | B2 | 2/2025 | Highsmith et al. |
| 12,221,163 | B2 | 2/2025 | Günther et al. |
| 12,226,141 | B2 | 2/2025 | Yaffe et al. |
| 12,226,314 | B2 | 2/2025 | Reimer et al. |
| 12,232,755 | B2 | 2/2025 | Phan et al. |
| 12,232,874 | B2 | 2/2025 | Salazar et al. |
| 12,232,908 | B2 | 2/2025 | Stigall et al. |
| 12,239,364 | B2 | 3/2025 | Govari et al. |
| 12,246,143 | B2 | 3/2025 | Leeflang et al. |
| 12,251,224 | B2 | 3/2025 | Selkee et al. |
| 12,256,913 | B2 | 3/2025 | Nunan |
| 12,256,984 | B2 | 3/2025 | Ku et al. |
| 12,256,985 | B2 | 3/2025 | Zhou et al. |
| 12,263,014 | B2 | 4/2025 | Tegg et al. |
| 12,263,338 | B2 | 4/2025 | de la Rama et al. |
| 12,268,456 | B2 | 4/2025 | Harlev et al. |
| 12,290,646 | B2 | 5/2025 | Osypka et al. |
| 12,310,715 | B2 | 5/2025 | Hoitink et al. |
| D1,078,039 | S | 6/2025 | Tegg et al. |
| 12,324,620 | B2 | 6/2025 | de la Rama et al. |
| 12,337,124 | B2 | 6/2025 | Campbell et al. |

(56)     References Cited

U.S. PATENT DOCUMENTS

| | | |
|---|---|---|
| 2002/0165484 A1 | 11/2002 | Bowe et al. |
| 2005/0159741 A1 | 7/2005 | Paul et al. |
| 2009/0198300 A1 | 8/2009 | Zhang et al. |
| 2011/0118726 A1 | 5/2011 | de la Rama et al. |
| 2012/0271302 A1 | 10/2012 | Behl et al. |
| 2012/0296232 A1 | 11/2012 | Ng |
| 2013/0102869 A1* | 4/2013 | Kordis ................. A61B 5/6859 |
| | | 600/375 |
| 2013/0172715 A1 | 7/2013 | Just et al. |
| 2013/0253504 A1 | 9/2013 | Fang |
| 2013/0274582 A1 | 10/2013 | Afonso et al. |
| 2014/0100639 A1 | 4/2014 | Lee et al. |
| 2014/0200639 A1 | 7/2014 | de la Rama |
| 2014/0269602 A1 | 9/2014 | Kawagishi |
| 2014/0296846 A1 | 10/2014 | Huszar et al. |
| 2014/0296902 A1 | 10/2014 | Huszar et al. |
| 2014/0316496 A1 | 10/2014 | Masson et al. |
| 2014/0336636 A1 | 11/2014 | Huszar et al. |
| 2014/0350564 A1 | 11/2014 | Huszar et al. |
| 2015/0001191 A1 | 1/2015 | Lee et al. |
| 2015/0011991 A1 | 1/2015 | Buysman et al. |
| 2015/0105645 A1 | 4/2015 | Subramaniam et al. |
| 2015/0119911 A1 | 4/2015 | Mckenzie |
| 2015/0141785 A1 | 5/2015 | Hayam et al. |
| 2015/0159741 A1 | 6/2015 | Versteyhe et al. |
| 2015/0223757 A1* | 8/2015 | Werneth ............... A61B 5/0205 |
| | | 600/301 |
| 2015/0351652 A1 | 12/2015 | Marecki et al. |
| 2016/0113582 A1* | 4/2016 | Altmann ............... A61M 25/09 |
| | | 606/41 |
| 2016/0143588 A1 | 5/2016 | Hoitink et al. |
| 2016/0213423 A1 | 7/2016 | Kauphusman et al. |
| 2016/0213916 A1 | 7/2016 | de la Rama |
| 2016/0278851 A1 | 9/2016 | Mannion et al. |
| 2016/0317094 A1 | 11/2016 | Byrd et al. |
| 2016/0331471 A1 | 11/2016 | Deno et al. |
| 2016/0331933 A1 | 11/2016 | Knutsen |
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 | 2/2017 | Deno et al. |
| 2017/0112404 A1 | 4/2017 | de la Rama et al. |
| 2017/0112405 A1 | 4/2017 | Sterrett et al. |
| 2017/0273738 A1 | 9/2017 | Wu |
| 2017/0319269 A1 | 11/2017 | Oliverius et al. |
| 2017/0367756 A1 | 12/2017 | Sliwa et al. |
| 2018/0042667 A1 | 2/2018 | Pappone et al. |
| 2018/0056038 A1 | 3/2018 | Aujla |
| 2018/0070845 A1 | 3/2018 | Hoitink et al. |
| 2018/0085064 A1 | 3/2018 | Auerbach et al. |
| 2018/0116539 A1 | 5/2018 | Olson et al. |
| 2018/0161093 A1 | 6/2018 | Basu et al. |
| 2018/0193089 A1 | 7/2018 | Wu |
| 2018/0229030 A1 | 8/2018 | Dubuclet et al. |
| 2018/0235496 A1 | 8/2018 | Wu et al. |
| 2018/0303361 A1 | 10/2018 | Wu et al. |
| 2018/0335519 A1 | 11/2018 | Gliner et al. |
| 2018/0369574 A1 | 12/2018 | Dubuclet et al. |
| 2019/0009052 A1 | 1/2019 | Oliverius et al. |
| 2019/0125378 A1 | 5/2019 | Shelton, IV et al. |
| 2019/0175043 A1 | 6/2019 | Wu et al. |
| 2019/0192826 A1 | 6/2019 | Wada |
| 2019/0239812 A1 | 8/2019 | Botzer et al. |
| 2020/0000359 A1 | 1/2020 | de la Rama et al. |
| 2020/0054391 A1 | 2/2020 | Litscher et al. |
| 2020/0069365 A1 | 3/2020 | Harlev et al. |
| 2020/0077908 A1 | 3/2020 | Hagfors et al. |
| 2020/0077912 A1 | 3/2020 | Wu et al. |
| 2020/0113469 A1 | 4/2020 | Sahadevan et al. |
| 2020/0121894 A1 | 4/2020 | Prabhu et al. |
| 2020/0138334 A1 | 5/2020 | Hill et al. |
| 2020/0138378 A1 | 5/2020 | de la Rama et al. |
| 2020/0155021 A1 | 5/2020 | Wu et al. |
| 2020/0205737 A1 | 7/2020 | Beeckler |
| 2020/0214635 A1 | 7/2020 | Dahlen et al. |
| 2020/0221966 A1 | 7/2020 | Wu et al. |
| 2020/0229727 A1 | 7/2020 | Hoitink et al. |
| 2020/0229866 A1 | 7/2020 | Harlev et al. |
| 2020/0253496 A1 | 8/2020 | Deno et al. |
| 2020/0305744 A1 | 10/2020 | Weerakoon et al. |
| 2020/0329989 A1 | 10/2020 | Aujla |
| 2020/0345262 A1 | 11/2020 | Selkee et al. |
| 2020/0360657 A1 | 11/2020 | Ganske |
| 2020/0398026 A1 | 12/2020 | Castelli et al. |
| 2020/0405166 A1 | 12/2020 | Wu et al. |
| 2021/0015551 A1 | 1/2021 | Fuentes-ortega et al. |
| 2021/0038860 A1 | 2/2021 | Mintz et al. |
| 2021/0059745 A1 | 3/2021 | Highsmith |
| 2021/0068693 A1 | 3/2021 | Fuentes-Ortega et al. |
| 2021/0077183 A1 | 3/2021 | Shubhayu et al. |
| 2021/0085920 A1 | 3/2021 | Roberts et al. |
| 2021/0085921 A1 | 3/2021 | Roberts et al. |
| 2021/0121231 A1 | 4/2021 | Basu et al. |
| 2021/0145342 A1 | 5/2021 | Wang |
| 2021/0153932 A1 | 5/2021 | Voth et al. |
| 2021/0187246 A1 | 6/2021 | Houck |
| 2021/0204871 A1 | 7/2021 | Goedeke et al. |
| 2021/0228136 A1 | 7/2021 | Fuentes-Ortega et al. |
| 2021/0228137 A1 | 7/2021 | Aujla |
| 2021/0267693 A1 | 9/2021 | Deno et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0361428 A1 | 11/2021 | Dixon |
| 2021/0369132 A1 | 12/2021 | Van Niekerk et al. |
| 2021/0369338 A1 | 12/2021 | Govari et al. |
| 2021/0369339 A1 | 12/2021 | Salazar et al. |
| 2021/0370022 A1 | 12/2021 | Bean et al. |
| 2021/0401345 A1 | 12/2021 | Wu et al. |
| 2021/0402148 A1 | 12/2021 | Beeckler et al. |
| 2022/0023594 A1 | 1/2022 | Pai |
| 2022/0054066 A1 | 2/2022 | Solis |
| 2022/0054198 A1 | 2/2022 | Tegg et al. |
| 2022/0061727 A1 | 3/2022 | Olson et al. |
| 2022/0071693 A1* | 3/2022 | Govari ................. A61B 5/6858 |
| 2022/0071704 A1 | 3/2022 | Le |
| 2022/0079496 A1 | 3/2022 | Squires et al. |
| 2022/0110675 A1 | 4/2022 | Govari et al. |
| 2022/0126063 A1 | 4/2022 | Weber |
| 2022/0175445 A1 | 6/2022 | Sutermeister et al. |
| 2022/0225941 A1 | 7/2022 | Smaill et al. |
| 2022/0226046 A1* | 7/2022 | Mariappan ............. A61B 5/063 |
| 2022/0265345 A1 | 8/2022 | Gottsche et al. |
| 2022/0273913 A1 | 9/2022 | Worley et al. |
| 2022/0313353 A1 | 10/2022 | Palushi et al. |
| 2022/0313961 A1 | 10/2022 | Tang |
| 2022/0331553 A1 | 10/2022 | Strom et al. |
| 2022/0354568 A1 | 11/2022 | Pappone et al. |
| 2022/0361942 A1 | 11/2022 | Lichter et al. |
| 2022/0370119 A1 | 11/2022 | Govari et al. |
| 2022/0370121 A1 | 11/2022 | Highsmith |
| 2022/0370122 A1 | 11/2022 | Smail |
| 2022/0370792 A1 | 11/2022 | De La Rama et al. |
| 2022/0387012 A1 | 12/2022 | Nunan |
| 2022/0387099 A1 | 12/2022 | Cohen et al. |
| 2022/0387100 A1 | 12/2022 | Greenbaum et al. |
| 2022/0395214 A1 | 12/2022 | Altman et al. |
| 2022/0401032 A1 | 12/2022 | Govari et al. |
| 2022/0401693 A1 | 12/2022 | Oliverius et al. |
| 2022/0409860 A1 | 12/2022 | Castelli et al. |
| 2023/0000415 A1 | 1/2023 | Olson |
| 2023/0000547 A1 | 1/2023 | Viswanathan et al. |
| 2023/0000548 A1 | 1/2023 | Viswanathan |
| 2023/0000550 A1 | 1/2023 | Nedved et al. |
| 2023/0001148 A1 | 1/2023 | Sharma |
| 2023/0008044 A1 | 1/2023 | Rao et al. |
| 2023/0009573 A1 | 1/2023 | Van Niekerk et al. |
| 2023/0011509 A1 | 1/2023 | Sterrett et al. |
| 2023/0012307 A1 | 1/2023 | Harlev et al. |
| 2023/0024690 A1 | 1/2023 | Cohen et al. |
| 2023/0028549 A1 | 1/2023 | Maierhofer et al. |
| 2023/0029648 A1 | 2/2023 | Niekerk et al. |
| 2023/0033444 A1 | 2/2023 | Knighton et al. |

(56) References Cited

U.S. PATENT DOCUMENTS

| | | |
|---|---|---|
| 2023/0035917 A1 | 2/2023 | Gutbrod et al. |
| 2023/0043627 A1 | 2/2023 | Tang et al. |
| 2023/0043978 A1 | 2/2023 | Govari |
| 2023/0046955 A1 | 2/2023 | Akagane |
| 2023/0049942 A1 | 2/2023 | Narayan et al. |
| 2023/0052130 A1 | 2/2023 | Govari et al. |
| 2023/0053064 A1 | 2/2023 | Altmann |
| 2023/0055089 A1 | 2/2023 | Govari et al. |
| 2023/0064082 A1 | 3/2023 | Sun et al. |
| 2023/0078216 A1 | 3/2023 | Govari |
| 2023/0083615 A1 | 3/2023 | Nguyen et al. |
| 2023/0084626 A1 | 3/2023 | Grunewald |
| 2023/0105390 A1 | 4/2023 | Gutbrod et al. |
| 2023/0105973 A1 | 4/2023 | Gutbrod et al. |
| 2023/0114222 A1 | 4/2023 | Esguerra Wilczynski et al. |
| 2023/0121397 A1 | 4/2023 | Oliverius et al. |
| 2023/0123266 A1 | 4/2023 | Castelli et al. |
| 2023/0149069 A1 | 5/2023 | Van Niekerk et al. |
| 2023/0149070 A1 | 5/2023 | Olson et al. |
| 2023/0149675 A1 | 5/2023 | Leung et al. |
| 2023/0172611 A1 | 6/2023 | Biscarrat et al. |
| 2023/0172659 A1 | 6/2023 | Olson et al. |
| 2023/0172661 A1 | 6/2023 | Harlev et al. |
| 2023/0190166 A1 | 6/2023 | Spector |
| 2023/0190198 A1 | 6/2023 | Pederson et al. |
| 2023/0190369 A1 | 6/2023 | Caples et al. |
| 2023/0200894 A1 | 6/2023 | Rodriguez et al. |
| 2023/0200895 A1 | 6/2023 | Ebrahimi et al. |
| 2023/0210433 A1 | 7/2023 | Abbas et al. |
| 2023/0264031 A1 | 8/2023 | Harlev et al. |
| 2023/0284956 A1 | 9/2023 | Wu et al. |
| 2023/0310071 A1 | 10/2023 | Van Niekerk et al. |
| 2023/0329577 A1 | 10/2023 | Cao et al. |
| 2023/0329618 A1 | 10/2023 | Wu et al. |
| 2023/0329784 A1 | 10/2023 | Stewart et al. |
| 2023/0337956 A1 | 10/2023 | Rodriguez Soto |
| 2023/0346455 A1 | 11/2023 | Beeckler et al. |
| 2023/0380746 A1 | 11/2023 | Van Niekerk et al. |
| 2023/0404657 A1 | 12/2023 | Olson |
| 2023/0405338 A1 | 12/2023 | Botzer |
| 2023/0414156 A1 | 12/2023 | Liu et al. |
| 2024/0008920 A1 | 1/2024 | Govari et al. |
| 2024/0023865 A1 | 1/2024 | Wong et al. |
| 2024/0033470 A1 | 2/2024 | Olson et al. |
| 2024/0057939 A1 | 2/2024 | Wang |
| 2024/0058073 A1 | 2/2024 | Govari |
| 2024/0065755 A1 | 2/2024 | Ebrahimi et al. |
| 2024/0081712 A1 | 3/2024 | Selkee et al. |
| 2024/0081905 A1 | 3/2024 | Corvi et al. |
| 2024/0123191 A1 | 4/2024 | Highsmith et al. |
| 2024/0173070 A1 | 5/2024 | Selkee et al. |
| 2024/0198054 A1 | 6/2024 | Schultz |
| 2024/0206966 A1 | 6/2024 | Kelly et al. |
| 2024/0207578 A1 | 6/2024 | Soltis et al. |
| 2024/0225726 A1 | 7/2024 | Govari et al. |
| 2024/0245360 A1 | 7/2024 | Gliner et al. |
| 2024/0252815 A1 | 8/2024 | de la Rama et al. |
| 2024/0277277 A1 | 8/2024 | Hoitink et al. |
| 2024/0306900 A1 | 9/2024 | Thissen et al. |
| 2024/0325691 A1 | 10/2024 | Bogusky |
| 2024/0350063 A1 | 10/2024 | Olson et al. |
| 2024/0350070 A1 | 10/2024 | Rodriguez |
| 2024/0366299 A1 | 11/2024 | Dando et al. |
| 2024/0366301 A1 | 11/2024 | Govari et al. |
| 2024/0415438 A1 | 12/2024 | Wu et al. |
| 2024/0423707 A1 | 12/2024 | Govari et al. |
| 2025/0009272 A1 | 1/2025 | de la Rama et al. |
| 2025/0017648 A1 | 1/2025 | Kim |
| 2025/0025231 A1 | 1/2025 | Oliverius et al. |
| 2025/0025296 A1 | 1/2025 | Rothfuss et al. |
| 2025/0025643 A1 | 1/2025 | Sigmon, Jr. et al. |
| 2025/0032028 A1 | 1/2025 | Deno et al. |
| 2025/0032181 A1 | 1/2025 | Harlev et al. |
| 2025/0032749 A1 | 1/2025 | Tao et al. |
| 2025/0040853 A1 | 2/2025 | Wu et al. |
| 2025/0040889 A1 | 2/2025 | Smaill et al. |
| 2025/0040955 A1 | 2/2025 | Murray et al. |
| 2025/0043590 A1 | 2/2025 | Furseth et al. |
| 2025/0049460 A1 | 2/2025 | Worrell et al. |
| 2025/0057595 A1 | 2/2025 | Narayan et al. |
| 2025/0064430 A1 | 2/2025 | Mantri et al. |
| 2025/0064512 A1 | 2/2025 | Kasher et al. |
| 2025/0064585 A1 | 2/2025 | Vidlund et al. |
| 2025/0072897 A1 | 3/2025 | Reu et al. |
| 2025/0082438 A1 | 3/2025 | Seeralan et al. |
| 2025/0082901 A1 | 3/2025 | Govari et al. |
| 2025/0082903 A1 | 3/2025 | Hsueh et al. |
| 2025/0090070 A1 | 3/2025 | Wu et al. |
| 2025/0090151 A1 | 3/2025 | Pedersen et al. |
| 2025/0090225 A1 | 3/2025 | Savastano et al. |
| 2025/0090807 A1 | 3/2025 | Padilla et al. |
| 2025/0099176 A1 | 3/2025 | Kim et al. |
| 2025/0127567 A1 | 4/2025 | Highsmith |
| 2025/0152104 A1 | 5/2025 | Tegg et al. |
| 2025/0152932 A1 | 5/2025 | de la Rama et al. |
| 2025/0160942 A1 | 5/2025 | Ku et al. |
| 2025/0177037 A1 | 6/2025 | Olson et al. |
| 2025/0185968 A1 | 6/2025 | Salazar et al. |
| 2025/0185969 A1 | 6/2025 | Selkee et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101797181 A | 8/2010 |
| CN | 101927053 B | 1/2015 |
| CN | 103157168 B | 4/2015 |
| CN | 105960201 A | 9/2016 |
| CN | 106859765 A | 6/2017 |
| CN | 106901831 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 105960200 B | 8/2019 |
| CN | 105451680 B | 10/2019 |
| CN | 110536646 A | 12/2019 |
| CN | 110604860 A | 12/2019 |
| CN | 105960201 B | 3/2020 |
| CN | 111225627 A | 6/2020 |
| CN | 111227929 A | 6/2020 |
| CN | 111374755 A | 7/2020 |
| CN | 111432739 A | 7/2020 |
| CN | 111657866 A | 9/2020 |
| CN | 111839499 A | 10/2020 |
| CN | 106264715 B | 11/2020 |
| CN | 106264716 B | 11/2020 |
| CN | 112040861 A | 12/2020 |
| CN | 106308790 B | 6/2021 |
| CN | 107529958 B | 7/2021 |
| CN | 109310469 B | 7/2021 |
| CN | 213665310 U | 7/2021 |
| CN | 213821695 U | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 113939327 A | 1/2022 |
| CN | 108289709 B | 3/2022 |
| CN | 114126522 A | 3/2022 |
| CN | 114343831 A | 4/2022 |
| CN | 114375211 A | 4/2022 |
| CN | 216257368 U | 4/2022 |
| CN | 114424971 A | 5/2022 |
| CN | 111246907 B | 7/2022 |
| CN | 114727815 A | 7/2022 |
| CN | 114828745 A | 7/2022 |

(56)     References Cited

FOREIGN PATENT DOCUMENTS

| | | | |
|---|---|---|---|
| CN | 107773300 B | 8/2022 |
| CN | 108567424 B | 8/2022 |
| CN | 114903491 A | 8/2022 |
| CN | 106859638 B | 10/2022 |
| CN | 108283520 B | 10/2022 |
| CN | 110547865 B | 10/2022 |
| CN | 115137944 A | 10/2022 |
| CN | 107343816 B | 11/2022 |
| CN | 113545841 B | 11/2022 |
| CN | 115281680 A | 11/2022 |
| CN | 115363736 A | 11/2022 |
| CN | 115363746 A | 11/2022 |
| CN | 115364333 A | 11/2022 |
| CN | 115379873 A | 11/2022 |
| CN | 217793303 U | 11/2022 |
| CN | 115426941 A | 12/2022 |
| CN | 115444544 A | 12/2022 |
| CN | 115444549 A | 12/2022 |
| CN | 115461007 A | 12/2022 |
| CN | 115500932 A | 12/2022 |
| CN | 115500933 A | 12/2022 |
| CN | 217938222 U | 12/2022 |
| CN | 115590606 A | 1/2023 |
| CN | 115590608 A | 1/2023 |
| CN | 115666700 A | 1/2023 |
| CN | 107343784 B | 2/2023 |
| CN | 115697221 A | 2/2023 |
| CN | 115702823 A | 2/2023 |
| CN | 115768346 A | 3/2023 |
| CN | 115886978 A | 4/2023 |
| CN | 115942915 A | 4/2023 |
| CN | 115990309 A | 4/2023 |
| CN | 110520067 B | 5/2023 |
| CN | 111225627 B | 5/2023 |
| CN | 116115323 A | 5/2023 |
| CN | 116135163 A | 5/2023 |
| CN | 116137804 A | 5/2023 |
| CN | 116157084 A | 5/2023 |
| CN | 116157174 A | 5/2023 |
| CN | 116158839 A | 5/2023 |
| CN | 219022916 U | 5/2023 |
| CN | 106419897 B | 6/2023 |
| CN | 111065350 B | 6/2023 |
| CN | 116234511 A | 6/2023 |
| CN | 116250914 A | 6/2023 |
| CN | 116327346 A | 6/2023 |
| CN | 109259854 B | 10/2023 |
| CN | 111657866 B | 10/2023 |
| CN | 117122328 A | 11/2023 |
| CN | 117355271 A | 1/2024 |
| CN | 117357121 A | 1/2024 |
| CN | 117396150 A | 1/2024 |
| CN | 117426866 A | 1/2024 |
| CN | 114209331 B | 2/2024 |
| CN | 117582284 A | 2/2024 |
| CN | 117597080 A | 2/2024 |
| CN | 111836579 B | 3/2024 |
| CN | 112704546 B | 3/2024 |
| CN | 117897110 A | 4/2024 |
| CN | 117942483 A | 4/2024 |
| CN | 117958829 A | 5/2024 |
| CN | 115379873 B | 6/2024 |
| CN | 118234442 A | 6/2024 |
| CN | 118251185 A | 6/2024 |
| CN | 111096749 B | 7/2024 |
| CN | 113164127 B | 7/2024 |
| CN | 118384409 A | 7/2024 |
| CN | 113993572 B | 8/2024 |
| CN | 114040724 B | 8/2024 |
| CN | 111683581 B | 9/2024 |
| CN | 112040861 B | 9/2024 |
| CN | 118697365 A | 9/2024 |
| CN | 118715039 A | 9/2024 |
| CN | 111683614 B | 10/2024 |
| CN | 112121284 B | 11/2024 |
| CN | 118891015 A | 11/2024 |
| CN | 118900667 A | 11/2024 |
| CN | 113226443 B | 12/2024 |
| CN | 115381549 B | 12/2024 |
| CN | 111374755 B | 1/2025 |
| CN | 111436928 B | 1/2025 |
| CN | 113543728 B | 1/2025 |
| CN | 113693716 B | 1/2025 |
| CN | 114340535 B | 1/2025 |
| CN | 115284943 B | 1/2025 |
| CN | 115338627 B | 1/2025 |
| CN | 119255743 A | 1/2025 |
| CN | 119255832 A | 1/2025 |
| CN | 119384251 A | 1/2025 |
| CN | 111691972 B | 2/2025 |
| CN | 112278762 B | 2/2025 |
| CN | 112520267 B | 2/2025 |
| CN | 112674068 B | 2/2025 |
| CN | 115252012 B | 2/2025 |
| CN | 119385661 A | 2/2025 |
| CN | 119455229 A | 2/2025 |
| CN | 119497601 A | 2/2025 |
| CN | 119522063 A | 2/2025 |
| CN | 111462635 B | 3/2025 |
| CN | 112207374 B | 3/2025 |
| CN | 119584942 A | 3/2025 |
| CN | 119607406 A | 3/2025 |
| CN | 119730804 A | 3/2025 |
| CN | 112040860 B | 5/2025 |
| CN | 114423344 B | 5/2025 |
| CN | 111374756 B | 6/2025 |
| CN | 112135576 B | 6/2025 |
| CN | 115461007 B | 6/2025 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2664295 A1 | 11/2013 |
| EP | 2604306 B1 | 1/2014 |
| EP | 2732843 A1 | 5/2014 |
| EP | 2747680 A2 | 7/2014 |
| EP | 2752153 A1 | 7/2014 |
| EP | 2907462 A1 | 8/2015 |
| EP | 2915555 A1 | 9/2015 |
| EP | 1968679 B1 | 9/2016 |
| EP | 2241279 B1 | 9/2016 |
| EP | 3111872 A1 | 1/2017 |
| EP | 2796103 B1 | 2/2017 |
| EP | 3222209 A1 | 9/2017 |
| EP | 2792322 B1 | 10/2017 |
| EP | 2792323 B1 | 10/2017 |
| EP | 3115076 A4 | 10/2017 |
| EP | 3117863 A4 | 10/2017 |
| EP | 3030182 B1 | 1/2018 |
| EP | 3287092 A1 | 2/2018 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3345540 A1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 3403571 A1 | 11/2018 |
| EP | 1759668 B1 | 12/2018 |
| EP | 3020352 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3073908 B1 | 4/2019 |
| EP | 3466363 A1 | 4/2019 |
| EP | 2550989 B1 | 6/2019 |
| EP | 3512589 A1 | 7/2019 |

(56) References Cited

FOREIGN PATENT DOCUMENTS

| | | | |
|---|---|---|---|
| EP | 3512590 | A1 | 7/2019 |
| EP | 3527125 | A1 | 8/2019 |
| EP | 3531903 | A1 | 9/2019 |
| EP | 3581229 | A1 | 12/2019 |
| EP | 3434218 | B1 | 2/2020 |
| EP | 2908723 | B1 | 3/2020 |
| EP | 3335658 | B1 | 4/2020 |
| EP | 3073907 | B1 | 6/2020 |
| EP | 3673851 | A1 | 7/2020 |
| EP | 3114987 | B1 | 8/2020 |
| EP | 3178516 | B1 | 9/2020 |
| EP | 3708104 | A1 | 9/2020 |
| EP | 3711662 | A1 | 9/2020 |
| EP | 3721796 | A1 | 10/2020 |
| EP | 3733103 | A1 | 11/2020 |
| EP | 3738508 | A1 | 11/2020 |
| EP | 3738509 | A1 | 11/2020 |
| EP | 3340916 | B1 | 12/2020 |
| EP | 3579908 | B1 | 12/2020 |
| EP | 3749174 | A1 | 12/2020 |
| EP | 3749191 | A1 | 12/2020 |
| EP | 3749192 | A1 | 12/2020 |
| EP | 3749195 | A1 | 12/2020 |
| EP | 3750475 | A1 | 12/2020 |
| EP | 3768185 | A1 | 1/2021 |
| EP | 2155301 | B1 | 4/2021 |
| EP | 3432820 | B1 | 4/2021 |
| EP | 3476331 | B1 | 5/2021 |
| EP | 3579758 | B1 | 5/2021 |
| EP | 2809254 | B1 | 6/2021 |
| EP | 3508245 | B1 | 7/2021 |
| EP | 3858277 | A1 | 8/2021 |
| EP | 3892221 | A1 | 10/2021 |
| EP | 3902461 | A1 | 11/2021 |
| EP | 3915477 | A1 | 12/2021 |
| EP | 3915501 | A1 | 12/2021 |
| EP | 3919014 | A1 | 12/2021 |
| EP | 3932343 | A4 | 1/2022 |
| EP | 3791820 | B9 | 4/2022 |
| EP | 3986520 | A1 | 4/2022 |
| EP | 3991680 | A2 | 5/2022 |
| EP | 3995079 | A1 | 5/2022 |
| EP | 4000506 | A1 | 5/2022 |
| EP | 3153124 | B1 | 7/2022 |
| EP | 3860447 | A4 | 7/2022 |
| EP | 4025112 | A1 | 7/2022 |
| EP | 4031007 | A1 | 7/2022 |
| EP | 4031044 | A2 | 7/2022 |
| EP | 4039215 | A1 | 8/2022 |
| EP | 4041112 | A1 | 8/2022 |
| EP | 3363397 | B1 | 9/2022 |
| EP | 3673944 | B1 | 9/2022 |
| EP | 3915501 | B1 | 9/2022 |
| EP | 3949848 | A4 | 9/2022 |
| EP | 4076193 | A1 | 10/2022 |
| EP | 4078255 | A1 | 10/2022 |
| EP | 4079365 | A2 | 10/2022 |
| EP | 3609414 | B1 | 11/2022 |
| EP | 4088676 | A1 | 11/2022 |
| EP | 4091565 | A1 | 11/2022 |
| EP | 4091569 | A1 | 11/2022 |
| EP | 4093274 | A1 | 11/2022 |
| EP | 4096545 | A1 | 12/2022 |
| EP | 4101372 | A1 | 12/2022 |
| EP | 4101375 | A1 | 12/2022 |
| EP | 4101383 | A1 | 12/2022 |
| EP | 4104763 | A1 | 12/2022 |
| EP | 4106625 | A1 | 12/2022 |
| EP | 4106853 | A2 | 12/2022 |
| EP | 2844193 | B1 | 1/2023 |
| EP | 3100696 | B1 | 1/2023 |
| EP | 3166524 | B1 | 1/2023 |
| EP | 3946123 | A4 | 1/2023 |
| EP | 4115832 | A1 | 1/2023 |
| EP | 4115833 | A1 | 1/2023 |
| EP | 4115936 | A1 | 1/2023 |
| EP | 4120963 | A1 | 1/2023 |
| EP | 4122414 | A1 | 1/2023 |
| EP | 4134032 | A1 | 2/2023 |
| EP | 4137080 | A1 | 2/2023 |
| EP | 3115076 | B1 | 3/2023 |
| EP | 3658054 | B1 | 3/2023 |
| EP | 4144397 | A1 | 3/2023 |
| EP | 4157420 | A1 | 4/2023 |
| EP | 4159124 | A1 | 4/2023 |
| EP | 4164519 | A1 | 4/2023 |
| EP | 4167886 | A1 | 4/2023 |
| EP | 4179991 | A1 | 5/2023 |
| EP | 4181810 | A1 | 5/2023 |
| EP | 4185224 | A1 | 5/2023 |
| EP | 4185225 | A1 | 5/2023 |
| EP | 2803329 | B1 | 6/2023 |
| EP | 3015064 | B1 | 6/2023 |
| EP | 3141183 | B1 | 6/2023 |
| EP | 3398549 | B1 | 6/2023 |
| EP | 3768185 | B1 | 6/2023 |
| EP | 4190232 | A1 | 6/2023 |
| EP | 4190257 | A2 | 6/2023 |
| EP | 4193947 | A1 | 6/2023 |
| EP | 4201356 | A2 | 6/2023 |
| EP | 4201357 | A1 | 6/2023 |
| EP | 4205684 | A1 | 7/2023 |
| EP | 4218579 | A1 | 8/2023 |
| EP | 2816966 | B1 | 10/2023 |
| EP | 3113671 | B1 | 10/2023 |
| EP | 3681427 | B1 | 10/2023 |
| EP | 3738509 | B1 | 10/2023 |
| EP | 3749195 | B1 | 10/2023 |
| EP | 4257068 | A1 | 10/2023 |
| EP | 4265210 | A1 | 10/2023 |
| EP | 3209234 | B1 | 11/2023 |
| EP | 3527125 | B1 | 11/2023 |
| EP | 3721796 | B1 | 11/2023 |
| EP | 3731747 | B1 | 11/2023 |
| EP | 3998935 | B1 | 11/2023 |
| EP | 4091547 | B1 | 11/2023 |
| EP | 4233699 | A3 | 11/2023 |
| EP | 4268746 | A1 | 11/2023 |
| EP | 4272631 | A2 | 11/2023 |
| EP | 4285850 | A1 | 12/2023 |
| EP | 4291123 | A1 | 12/2023 |
| EP | 3192442 | B1 | 1/2024 |
| EP | 3892221 | B1 | 1/2024 |
| EP | 4298995 | A2 | 1/2024 |
| EP | 4309606 | A1 | 1/2024 |
| EP | 3738508 | B1 | 2/2024 |
| EP | 4324388 | A1 | 2/2024 |
| EP | 4327768 | A1 | 2/2024 |
| EP | 4137051 | B1 | 3/2024 |
| EP | 4340762 | A1 | 3/2024 |
| EP | 3124069 | B1 | 4/2024 |
| EP | 4003234 | B9 | 4/2024 |
| EP | 4159124 | B1 | 4/2024 |
| EP | 3943139 | B1 | 5/2024 |
| EP | 4167886 | B1 | 5/2024 |
| EP | 4342406 | A3 | 5/2024 |
| EP | 4353171 | A3 | 5/2024 |
| EP | 4360572 | A1 | 5/2024 |
| EP | 4362831 | A1 | 5/2024 |
| EP | 4364680 | A2 | 5/2024 |
| EP | 4364765 | A2 | 5/2024 |
| EP | 4370064 | A1 | 5/2024 |
| EP | 3498156 | B1 | 6/2024 |
| EP | 4044947 | B1 | 6/2024 |
| EP | 4344722 | A3 | 6/2024 |
| EP | 4376745 | A1 | 6/2024 |
| EP | 4378515 | A2 | 6/2024 |
| EP | 3573559 | B1 | 7/2024 |
| EP | 3834728 | | 7/2024 |
| EP | 4392113 | A1 | 7/2024 |
| EP | 3603493 | B1 | 8/2024 |
| EP | 3998975 | B1 | 8/2024 |
| EP | 4205685 | B1 | 8/2024 |
| EP | 4412547 | A1 | 8/2024 |

(56) References Cited

FOREIGN PATENT DOCUMENTS

| | | | |
|---|---|---|---|
| EP | 4412549 | A1 | 8/2024 |
| EP | 4417112 | A2 | 8/2024 |
| EP | 3629964 | B1 | 9/2024 |
| EP | 4427666 | A2 | 9/2024 |
| EP | 4433133 | A1 | 9/2024 |
| EP | 4433141 | A1 | 9/2024 |
| EP | 3184035 | B1 | 10/2024 |
| EP | 4218579 | B1 | 10/2024 |
| EP | 4444195 | A1 | 10/2024 |
| EP | 4452069 | A1 | 10/2024 |
| EP | 3915477 | B1 | 11/2024 |
| EP | 4193947 | B1 | 11/2024 |
| EP | 4311484 | B1 | 11/2024 |
| EP | 3860447 | B1 | 12/2024 |
| EP | 4101372 | B1 | 12/2024 |
| EP | 4215138 | B1 | 12/2024 |
| EP | 4437989 | A3 | 12/2024 |
| EP | 4477171 | A2 | 12/2024 |
| EP | 3737453 | B1 | 1/2025 |
| EP | 3760152 | B1 | 1/2025 |
| EP | 3957968 | B1 | 1/2025 |
| EP | 4031044 | | 1/2025 |
| EP | 4311485 | | 1/2025 |
| EP | 4458292 | A3 | 1/2025 |
| EP | 4482412 | A1 | 1/2025 |
| EP | 4482413 | A1 | 1/2025 |
| EP | 4482564 | A2 | 1/2025 |
| EP | 4489634 | A1 | 1/2025 |
| EP | 4496546 | A1 | 1/2025 |
| EP | 2915555 | B1 | 2/2025 |
| EP | 4031007 | B1 | 2/2025 |
| EP | 4153526 | B1 | 2/2025 |
| EP | 4480435 | A3 | 2/2025 |
| EP | 4498955 | A1 | 2/2025 |
| EP | 4501285 | A1 | 2/2025 |
| EP | 4504085 | A1 | 2/2025 |
| EP | 4507562 | A1 | 2/2025 |
| EP | 4507582 | A1 | 2/2025 |
| EP | 4507607 | A1 | 2/2025 |
| EP | 4511098 | A2 | 2/2025 |
| EP | 451 4256 | A1 | 3/2025 |
| EP | 4483828 | A3 | 3/2025 |
| EP | 4514274 | A1 | 3/2025 |
| EP | 4387547 | B1 | 5/2025 |
| EP | 4370187 | B1 | 6/2025 |
| EP | 4555953 | A3 | 6/2025 |
| IL | 246415 | B | 12/2019 |
| IN | 201614021431 | A | 12/2016 |
| IN | 201614021432 | A | 12/2016 |
| IN | 201614021450 | A | 12/2016 |
| JP | 4545384 | B2 | 7/2010 |
| JP | 4887810 | B2 | 2/2012 |
| JP | 4940332 | B2 | 3/2012 |
| JP | 2012055602 | A | 3/2012 |
| JP | 2012200509 | A | 10/2012 |
| JP | 5154031 | B2 | 2/2013 |
| JP | 5193190 | B2 | 5/2013 |
| JP | 5372314 | B2 | 12/2013 |
| JP | 2014014713 | A | 1/2014 |
| JP | 5550150 | B2 | 5/2014 |
| JP | 5762697 | B2 | 6/2015 |
| JP | 5856712 | B2 | 2/2016 |
| JP | 5908270 | B2 | 4/2016 |
| JP | 5944331 | B2 | 7/2016 |
| JP | 6050522 | B2 | 12/2016 |
| JP | 6059737 | B2 | 12/2016 |
| JP | 2017012750 | A | 1/2017 |
| JP | 2017012755 | A | 1/2017 |
| JP | 2017038919 | A | 2/2017 |
| JP | 2017051211 | A | 3/2017 |
| JP | 2017104552 | A | 6/2017 |
| JP | 6246742 | B2 | 12/2017 |
| JP | 6342524 | B2 | 6/2018 |
| JP | 6434495 | B2 | 12/2018 |
| JP | 6445509 | B2 | 12/2018 |
| JP | 6445742 | B1 | 12/2018 |
| JP | 6466114 | B2 | 2/2019 |
| JP | 6479005 | B2 | 2/2019 |
| JP | 6515084 | B2 | 5/2019 |
| JP | 6528010 | B1 | 6/2019 |
| JP | 6655655 | B2 | 2/2020 |
| JP | 2020108766 | A | 7/2020 |
| JP | 6746734 | B2 | 8/2020 |
| JP | 6776021 | B2 | 10/2020 |
| JP | 6776025 | B2 | 10/2020 |
| JP | 6786275 | B2 | 11/2020 |
| JP | 6821812 | B2 | 1/2021 |
| JP | 2021007772 | A | 1/2021 |
| JP | 2021501011 | A | 1/2021 |
| JP | 6843502 | B2 | 3/2021 |
| JP | 2021069921 | A | 5/2021 |
| JP | 6894004 | B2 | 6/2021 |
| JP | 6920312 | B2 | 8/2021 |
| JP | 6926306 | B2 | 8/2021 |
| JP | 6932484 | B2 | 8/2021 |
| JP | 6936872 | B2 | 9/2021 |
| JP | 2021523755 | A | 9/2021 |
| JP | 6980386 | B2 | 12/2021 |
| JP | 2022020838 | A | 2/2022 |
| JP | 2022063862 | A | 4/2022 |
| JP | 7101228 | B2 | 7/2022 |
| JP | 7102558 | B2 | 7/2022 |
| JP | 7106301 | B2 | 7/2022 |
| JP | 7135202 | B2 | 9/2022 |
| JP | 2022540496 | A | 9/2022 |
| JP | 2022159146 | A | 10/2022 |
| JP | 2022176157 | A | 11/2022 |
| JP | 2022546719 | A | 11/2022 |
| JP | 2022548944 | A | 11/2022 |
| JP | 2022177819 | A | 12/2022 |
| JP | 2022179432 | A | 12/2022 |
| JP | 2022187485 | A | 12/2022 |
| JP | 2022187486 | A | 12/2022 |
| JP | 2022188763 | A | 12/2022 |
| JP | 2023002720 | A | 1/2023 |
| JP | 2023010544 | A | 1/2023 |
| JP | 2023501756 | A | 1/2023 |
| JP | 7220242 | B2 | 2/2023 |
| JP | 7230168 | B2 | 2/2023 |
| JP | 2023024395 | A | 2/2023 |
| JP | 2023026388 | A | 2/2023 |
| JP | 2023506505 | A | 2/2023 |
| JP | 2023507412 | A | 2/2023 |
| JP | 7242665 | B2 | 3/2023 |
| JP | 7242816 | B2 | 3/2023 |
| JP | 7246319 | B2 | 3/2023 |
| JP | 2023027023 | A | 3/2023 |
| JP | 2023027202 | A | 3/2023 |
| JP | 2023033335 | A | 3/2023 |
| JP | 7256621 | B2 | 4/2023 |
| JP | 7262919 | B2 | 4/2023 |
| JP | 2023515798 | A | 4/2023 |
| JP | 2023517284 | A | 4/2023 |
| JP | 7275333 | B2 | 5/2023 |
| JP | 7282759 | B2 | 5/2023 |
| JP | 2023074000 | A | 5/2023 |
| JP | 2023519039 | A | 5/2023 |
| JP | 7292822 | B2 | 6/2023 |
| JP | 2023526907 | A | 6/2023 |
| JP | 2023139173 | A | 10/2023 |
| JP | 7391562 | B2 | 11/2023 |
| JP | 7394766 | B2 | 11/2023 |
| JP | 2023160789 | A | 11/2023 |
| JP | 2023164368 | A | 11/2023 |
| JP | 7400050 | B2 | 12/2023 |
| JP | 2023177311 | A | 12/2023 |
| JP | 7423550 | B2 | 1/2024 |
| JP | 2024012693 | A | 1/2024 |
| JP | 2024014846 | A | 2/2024 |
| JP | 2024028213 | A | 3/2024 |
| JP | 2024031886 | A | 3/2024 |
| JP | 7465944 | B2 | 4/2024 |
| JP | 2024045056 | A | 4/2024 |
| JP | 2024046636 | A | 4/2024 |

(56) References Cited

FOREIGN PATENT DOCUMENTS

| | | | |
|---|---|---|---|
| JP | 2024059810 | A | 5/2024 |
| JP | 2024060605 | A | 5/2024 |
| JP | 7493935 | B2 | 6/2024 |
| JP | 7499702 | B2 | 6/2024 |
| JP | 7512156 | B2 | 7/2024 |
| JP | 7514764 | B2 | 7/2024 |
| JP | 7515637 | B2 | 7/2024 |
| JP | 7516185 | B2 | 7/2024 |
| JP | 7523073 | B2 | 7/2024 |
| JP | 7523074 | B2 | 7/2024 |
| JP | 2024528078 | A | 7/2024 |
| JP | 7517994 | B2 | 8/2024 |
| JP | 7520967 | B2 | 8/2024 |
| JP | 7530317 | B2 | 8/2024 |
| JP | 7532506 | B2 | 8/2024 |
| JP | 7535097 | B2 | 8/2024 |
| JP | 2024103761 | A | 8/2024 |
| JP | 7539974 | B2 | 9/2024 |
| JP | 7551326 | B2 | 9/2024 |
| JP | 2024121015 | A | 9/2024 |
| JP | 2024125304 | A | 9/2024 |
| JP | 7566503 | B2 | 10/2024 |
| JP | 2024536350 | A | 10/2024 |
| JP | 2024536352 | A | 10/2024 |
| JP | 2024537099 | A | 10/2024 |
| JP | 7574276 | B2 | 11/2024 |
| JP | 7577739 | B2 | 11/2024 |
| JP | 7587597 | B2 | 11/2024 |
| JP | 2024156696 | A | 11/2024 |
| JP | 2024543437 | A | 11/2024 |
| JP | 7592480 | B2 | 12/2024 |
| JP | 2024544543 | A | 12/2024 |
| JP | 7617073 | B2 | 1/2025 |
| JP | 7617103 | B2 | 1/2025 |
| JP | 2025013792 | A | 1/2025 |
| JP | 7628563 | B2 | 2/2025 |
| JP | 7633185 | B2 | 2/2025 |
| JP | 7637671 | B2 | 2/2025 |
| JP | 7639079 | B2 | 2/2025 |
| JP | 2025023950 | A | 2/2025 |
| JP | 2025026734 | A | 2/2025 |
| JP | 2025026852 | A | 2/2025 |
| JP | 2025027101 | A | 2/2025 |
| JP | 7635238 | B2 | 3/2025 |
| JP | 7640580 | B2 | 3/2025 |
| JP | 7641330 | B2 | 3/2025 |
| JP | 2025028941 | A | 3/2025 |
| JP | 2025036543 | A | 3/2025 |
| JP | 2025036738 | A | 3/2025 |
| JP | 2025507449 | A | 3/2025 |
| JP | 7646980 | B2 | 4/2025 |
| JP | 7647478 | B2 | 4/2025 |
| JP | 7654796 | B2 | 4/2025 |
| JP | 7662472 | B2 | 4/2025 |
| JP | 7662473 | B2 | 4/2025 |
| JP | 2025509157 | A | 4/2025 |
| JP | 2025511803 | A | 4/2025 |
| JP | 7686646 | B2 | 6/2025 |
| RU | 2016124794 | A | 12/2017 |
| RU | 2016124801 | A | 12/2017 |
| RU | 2016125763 | A | 1/2018 |
| WO | 9843530 | A1 | 10/1998 |
| WO | 0168178 | A1 | 9/2001 |
| WO | 2008091197 | A1 | 7/2008 |
| WO | 2014113612 | A1 | 7/2014 |
| WO | 2015057521 | A1 | 4/2015 |
| WO | 2015095577 | A1 | 6/2015 |
| WO | 2015130824 | A1 | 9/2015 |
| WO | 2016001015 | A1 | 1/2016 |
| WO | 2017098198 | A1 | 6/2017 |
| WO | 2018053148 | A1 | 3/2018 |
| WO | 2018053164 | A1 | 3/2018 |
| WO | 2018136741 | A1 | 7/2018 |
| WO | 2019195439 | A1 | 10/2019 |
| WO | 2019226640 | A1 | 11/2019 |
| WO | 2021053482 | A1 | 3/2021 |
| WO | 2021053648 | A1 | 3/2021 |
| WO | 2021061198 | A1 | 4/2021 |
| WO | 2021242852 | A1 | 12/2021 |
| WO | 2022038546 | A1 | 2/2022 |
| WO | 2022148153 | A1 | 7/2022 |
| WO | 2022180046 | A1 | 9/2022 |
| WO | 2022214870 | A1 | 10/2022 |
| WO | 2022246011 | A1 | 11/2022 |
| WO | 2022251429 | A1 | 12/2022 |
| WO | 2023275848 | A1 | 1/2023 |
| WO | 2023278577 | A1 | 1/2023 |
| WO | 2023280822 | A1 | 1/2023 |
| WO | 2023287289 | A1 | 1/2023 |
| WO | 2023007324 | A1 | 2/2023 |
| WO | 2023009569 | A1 | 2/2023 |
| WO | 2023018741 | A1 | 2/2023 |
| WO | 2023028531 | A1 | 3/2023 |
| WO | 2023059507 | A1 | 4/2023 |
| WO | 2023059509 | A1 | 4/2023 |
| WO | 2023086778 | A1 | 5/2023 |
| WO | 2023086865 | A1 | 5/2023 |
| WO | 2023105322 | A1 | 6/2023 |
| WO | 2023122183 | A1 | 6/2023 |
| WO | 2023164001 | A1 | 8/2023 |
| WO | 2023192858 | A1 | 10/2023 |
| WO | 2023196810 | A1 | 10/2023 |

* cited by examiner

HIGH DENSITY PADDLE CATHETER WITH DISTAL COUPLER AND DISTAL ELECTRODE

CROSS REFERENCE TO RELATED APPLICATION DATA

The present application claims the benefit under 35 USC § 119(e) of U.S. Provisional Application Nos. 63/410,758 filed Sep. 28, 2022, and 63/435,886 filed Dec. 29, 2022; the full disclosures which are incorporated herein by reference in their entirety for all purposes.

BACKGROUND

Electrophysiological (EP) catheters can be configured for use in diagnosing and/or treating cardiac arrythmias. A cardiac arrythmia may be manifest in one or more observable medical conditions including, for example, an irregular heart rate, loss of synchronous atrioventricular contractions, and inadequate flow of blood through a chamber of the heart, which can lead to a variety of symptomatic and/or asymptomatic ailments and even death. Electrical activity of a patient's heart can be measured and assessed to determine whether the patient's heart exhibits a pathological electrical condition(s) associated with the occurrence of the cardiac arrythmia. Following diagnosis of the pathological electrical condition(s), a suitable treatment(s) can be used to selectively alter the patient's heart tissue to reduce or eliminate the pathological electrical condition to reduce or eliminate occurrence of the cardiac arrythmia. The treatment can include, for example, radio frequency (RF) ablation, pulsed field ablation, cryoablation, laser ablation, chemical ablation, high-intensity focused ultrasound ablation, microwave ablation, and/or other ablation treatments.

BRIEF SUMMARY

The following presents a simplified summary of some embodiments of the invention to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Where the term "planar" or, similarly, "plane" or "coplanar" is used herein, it should be understood to refer to a topological plane. In other words, a "plane" may not be "flat" in a Cartesian coordinate system, but rather represents a two-dimensional distribution that is planar in a topological sense. Likewise, where the term "linear" is used herein, it should be understood to refer to a topological plane. In other words, a "linear" may not be "straight line" in a Cartesian coordinate system, but rather represents a one-dimensional distribution that is linear in a topological sense.

The high-density catheters described herein may include an electrode assembly that includes a planar two-dimensional array of electrodes and a distal coupler assembly. The distal coupler assembly can include a base member and a distal electrode coupled to the base member. In an example, the distal electrode and the base member may have a one-piece construction with holes for receiving splines. In another example, the base member may include frame slots and the distal electrode may be slidably mounting over the base member. In some embodiments, the base member can include frame slots for receiving spline frame assemblies of the electrode assembly while the distal electrode is positioned relative to the base member in an insertion configuration of the distal coupler assembly to accommodate insertion of the spline frame assemblies into the frame slots. The distal electrode can then be repositioned relative to the base member to put the distal couple assembly into a retention configuration in which the distal electrode retains the spline frame assemblies in the frame slots. For example, in many embodiments, the distal electrode can be slid over the base member to reconfigure the distal coupler assembly between the insertion configuration and the retention configuration that includes a distal electrode and a planar two-dimensional array of electrodes. In many embodiments, the base member and the distal electrode are made from different materials. In addition to the above-described mechanical functionality of the distal coupler assembly, the distal electrode can be made of a precious metal (e.g., platinum) without incurring significant cost of machining the base member from the precious metal.

The electrode assembly can include any suitable number of spline assemblies. For example, the electrode assembly can include a first spline assembly, a second spline assembly, and a third spline assembly. Each spline assembly can include an electrode support section that supports a linear sequence of the planar two-dimensional array of electrodes. For example, in some embodiments, the electrode assembly includes five electrode support sections spaced apart from each other so that the planar two-dimensional array of electrodes have a planar distribution. In some embodiments, the second spline assembly and the third spline assembly share a symmetrical configuration and have opposite orientations in the electrode assembly that differ by 180 degrees. In many embodiments, the first spline assembly is centrally located in the electrode assembly. The first spline assembly is coupled to a portion of the distal coupler assembly. Each of the second spline assembly and the third spline assembly extend through the distal coupler assembly so that the position of each of the second spline assembly and the third spline assembly is restrained relative to the first spline assembly. The distal coupler assembly is configured to accommodate relative sliding of end portions of the second and third spline assemblies through the base member so as to reduce stresses induced in the electrode assembly by collapsing the electrode assembly from an expanded configuration to a collapsed configuration in which the electrode assembly is advanced through a patient's vasculature into the patient's heart for deployment in the expanded configuration. Furthermore, the distal electrode on the base member can indicate proximity to the target are in the heart, before causing the electrode assembly in the expanded configuration.

Thus, in one aspect, a catheter includes an elongated catheter shaft and an electrode assembly including a distal coupler assembly including a distal electrode. In many embodiments, the electrode assembly includes a first spline assembly having a distal portion and first spline electrodes distributed along the first spline assembly, a second spline assembly having a distal portion and second spline electrodes distributed along the second spline assembly, and a distal coupler assembly. The distal coupler assembly includes a base member configured to receive the distal portions of the first and second spline assemblies, and a distal electrode. The base member defines an opening configured to receive the distal portion of the second spline assembly. The distal electrode is configured to be mounted to the base member to secure the distal portion of the second spline assembly within the opening (e.g., holes or slots). In many embodiments, the distal electrode is configured to transmit and receive electrical signals via a wire and the first spline assembly is configured to route the wire to a proximal end of the first spline assembly. In many embodiments, the base member includes a proximal shaft portion configured to receive and secure in place the distal portion of the first spline assembly, and a distal shaft portion including the opening to receive and secure in place the distal portion of the second spline assembly.

In many embodiments, the opening includes a frame slot with a circumferential opening having an axially extending width and a transversely extending length. The axially extending width of the circumferential opening is less than a maximum cross-sectional dimension of an understructure of the second spline assembly. The frame slot is configured to receive a minimum cross-section dimension of the distal portion of the second spline assembly and deliver the distal portion into the opening such that the distal portion can be rotated within the opening to secure the second spline assembly within the opening. The distal portion of the second spline assembly is rotated by approximately 90° within the opening such that the maximum cross-sectional dimension of the distal portion covers the frame slot to securely install the distal portion in the opening of the base member. In some embodiments, the opening is a cylindrical hole extending transversely along the distal shaft portion of the base member.

In many embodiments, the distal shaft portion of the base member includes an electrode receiving portion configured to securely receive the distal electrode between a distal end and a proximal end of the distal shaft portion of the base member. The electrode receiving portion of the distal shaft portion includes a shoulder at the distal end to prevent axial displacement of the distal electrode upon assembly. The electrode receiving portion of the base member includes a chamfer at the proximal end to slidably receive a cover over the distal portion of the first spline assembly and abut against a proximal end of the distal electrode to secure and prevent axial displacement of the distal electrode on the distal shaft portion. The base member includes a wire slot or hole at a proximal end to facilitate receiving and coupling an electrical wire to the distal electrode via welding.

In many embodiments, the proximal shaft portion includes a channel configured to receive the distal portion of the first spline assembly. In many embodiments, the first spline assembly includes an understructure with an enlarged distal end. The channel includes an enlarged recess sized to receive the enlarged distal end of the first spline assembly and secure the first spline assembly to the proximal shaft portion of the base member. The channel of the proximal shaft portion extends proximally and configured to route a wire from the distal electrode to a proximal end of the first spline assembly. The channel of the proximal shaft portion has a depth to receive a sensor to be coupled to the first spline assembly.

In many embodiments, the distal electrode is a hollow cylinder with axial slots extending from a distal end toward a proximal end. Each of the axial slots has a width and a length corresponding to the opening in the base member to facilitate slidably coupling of the distal electrode to the base member while the distal portion of the second spline assembly is secured in the opening.

In many embodiments, the catheter further includes a third spline assembly. The third spline includes a distal portion and third spline assembly electrodes distributed along the third spline assembly. The distal coupler assembly further includes a second opening configured to receive and secure the distal portion of the third spline assembly. The opening of the base member is spaced from the second opening of the base member and located distally from the second opening.

In many embodiments, the first spline assembly includes a first spline having the distal portion and a proximal portion, and the first spline electrodes include a first set of electrodes distributed between the proximal portion and the distal portion of the first spline. The second spline assembly includes a second spline having a distal portion and a proximal portion, and a third spline having a distal portion and a proximal portion. The distal portions of the second spline and the third spline are joined to form the distal portion of the second spline assembly. The second spline electrodes include a second set of electrodes distributed between the proximal portion and the distal portion of the second spline, and a third set of electrodes distributed between the proximal portion and the distal portion of the third spline. The third spline assembly includes a fourth spline having a distal portion and a proximal portion, a fifth spline having a distal portion and a proximal portion, a fourth set of electrodes distributed between the proximal portion and the distal portion of the fourth spline, and a fifth set of electrodes distributed between the proximal portion and the distal portion of the fifth spline. In many embodiments, each of the first set of electrodes, the second set of electrodes, the third set of electrodes, the fourth set of electrodes, and the fifth set of electrodes include at least 4 electrodes.

In many embodiments, the second spline assembly is disposed around the first spline assembly, and the third spline assembly is disposed around the second spline assembly. The second spline and the third spline are disposed on either side of the first spline. The fourth spline and the fifth spline are disposed on either side of the first spline.

In many embodiments, the catheter further includes a proximal connector. The first spline assembly further includes a proximal portion, which is attached to and extends distally from the proximal connector. The first spline electrodes are distributed between the proximal portion and the distal portion of the first spline assembly.

In many embodiments, the base member includes an electrically conductive portion that is coated with an insulation material to electrically isolate the electrically conductive portion from the distal electrode of the distal coupler assembly. The base member and the distal electrode are configured for performing bipolar pacing to a target tissue In another aspect, a catheter including an elongated catheter shaft, an electrode assembly with a distal coupler. The electrode assembly includes a first spline assembly, a second spline assembly and a distal coupler. The first spline assembly includes a distal portion and first spline electrodes distributed along the first spline assembly. The second spline assembly includes a distal portion and second spline electrodes distributed along the second spline assembly. The distal coupler includes a first portion and a second portion made of electrically conductive materials and electrically isolated from each other. The second portion is configured to receive the distal portion of the first spline assembly. The first portion defines an opening configured to securely receive the distal portion of the second spline assembly within the opening. The distal coupler is configured as a single piece component. The first portion is configured to convey a first signal and the second portion is configured to receive a second signal; the first signal being isolated from the second signal.

In some embodiments, the first portion of the distal coupler is coated with an insulation material to electrically isolate the first portion from the second portion of the distal coupler. The first portion and the second portion of the distal coupler are configured for performing bipolar pacing to a target tissue. The bipolar pacing of the target tissue is performed during an electrophysiology procedure.

In another aspect, a catheter system including an elongated catheter shaft, an electrode assembly, and controller circuitry communicatively coupled to the electrode assembly is provided. The electrode assembly includes a first spline assembly includes a first distal portion and first spline assembly electrodes distributed along the first spline assembly, a second spline assembly includes a second distal portion and second spline assembly electrodes distributed along the second spline assembly, a third spline assembly includes a third distal portion, third spline assembly electrodes distributed along the third spline assembly, and a distal coupler assembly.

In many embodiments, the distal coupler assembly includes a base member configured to couple the first spline assembly, the second spline assembly, and the third spline assembly, and a distal electrode. The base member defines a first opening and a second opening. The first opening is configured to receive and accommodate the second distal portion of the second spline assembly. The second opening is configured to receive and accommodate the third distal portion of the third spline assembly. The distal electrode is configured to be mounted to the base member to secure the second and third distal portions in the first opening and the second opening, respectively. The controller circuitry is communicatively coupled to the electrode assembly, the first spline assembly electrodes, the second spline assembly electrodes, and the distal electrode. The distal electrode sends electrical signals to the controller circuitry to determine a proximity of a distal end of the electrode assembly to a target tissue to facilitate accurate maneuvering of the electrode assembly around the target tissue.

In many embodiments, each of the first and second openings includes a frame slot with a circumferential opening having an axially extending width and a transversely extending length. The axially extending width is less than a maximum cross-sectional dimension of understructures of the second spline assembly, and wherein the axially extending width is less than a maximum cross-sectional dimension of an understructure of the third spline assembly. In many embodiments, the first spline assembly is centrally disposed, the second spline assembly is disposed on an outer side of the first spline assembly, and the third spline assembly is disposed on an outer side of the second spline assembly.

In many embodiments, the catheter system further includes a display communicatively coupled to the controller circuitry. The controller circuitry is configured to generate and display a map indicative of positioning of the electrode assembly within a heart. In many embodiments, the controller circuitry is configured to generate and display a map indicative of one or more electrical characteristics of tissue contacted by the distal electrode, the first spline assembly electrodes, the second spline assembly electrodes, the third spline assembly electrodes.

In many embodiments, the distal coupler is a two-piece component. The base member is electrically isolated from the distal electrode. The base member is coated with an insulation material to electrically isolate the base member from the distal electrode. The catheter is configured to sense bipolar electrocardiogram, perform bipolar pacing or perform bipolar tissue ablation to the target tissue based on signals transmitted by the base member and the distal electrode. The catheter is configured to perform electrocardiogram sensing, bipolar pacing or tissue ablation of the target tissue during electrophysiology procedure.

In another aspect, a catheter including an elongated catheter shaft, and an electrode assembly is provided. The electrode assembly is coupled to the catheter shaft. In many embodiments, the electrode assembly includes an inner spline assembly, an outer spline assembly, distal electrodes, magnetic sensors, and a distal coupler. The inner spline assembly includes a first spline, a second spline, a distal portion coupling the first spline and the second spline, and spline electrodes distributed along the first spline and the second spline respectively. The outer spline assembly includes a third spline, a fourth spline, a distal portion coupling the third spline and the fourth spline, and another set of spline electrodes distributed along the third spline and the fourth spline. The distal electrodes are disposed along the distal portion of the inner spline assembly or the distal portion of the outer spline assembly. The magnetic sensors are configured for generating output indicative of a position and/or an orientation of the electrode assembly with respect to a target area. The distal coupler assembly is configured to receive the distal portions of the inner spline assembly and the outer spline assembly.

In many embodiments, the distal electrodes are disposed on the distal portion of the inner spline assembly. Each of the distal electrodes are configured to transmit electrical signals related to pacing. The electrical signals related to pacing are transmitted in response to the position and/or the orientation information from the magnetic sensors. The magnetic sensors are disposed within the outer spline assembly.

In many embodiments, the outer spline assembly surrounds the inner spline assembly on two sides. The distal portion of the inner spline assembly is spaced from the distal portion of the outer spline assembly within the distal coupler. The distal portion of the inner spline assembly is angled relative to each of the first spline and the second spline. The distal portion of the outer spline assembly is angled relative to each of the third spline and the fourth spline.

In many embodiments, the electrode assembly further includes a center spline assembly disposed between the first spline and the second spline of the inner spline assembly. The center spline assembly includes a center spline and center spline electrodes distributed along the center spline. The center spline has a distal portion. The distal coupler is coupled to the distal portion of the center spline. The distal coupler further includes a distal electrode disposed on the distal coupler.

In another aspect, a catheter system includes an elongated catheter shaft, an electrode assembly coupled to the catheter shaft, and controller circuitry. The electrode assembly includes an inner spline assembly, an outer spline assembly, distal electrodes, magnetic sensors, and distal coupler. The inner spline assembly includes a first spline, a second spline, a distal portion coupling the first spline and the second spline, and spline electrodes distributed along the first spline and the second spline respectively. The outer spline assembly includes a third spline, a fourth spline, a distal portion coupling the third spline and the fourth spline, and another set of spline electrodes distributed along the third spline and the fourth spline. The distal electrodes disposed along the distal portion of the inner spline assembly or the distal portion of the outer spline assembly. The magnetic sensors are configured for generating output indicative of a position and/or an orientation of the electrode assembly with respect to a target area. The magnetic sensors are disposed within the outer spline assembly. The distal coupler assembly configured to receive the distal portions of the inner spline assembly and the outer spline assembly.

The controller circuitry is communicatively coupled to the distal electrodes and the magnetic sensors of the electrode assembly, wherein the distal electrode transmits electrical signals to and from the controller circuitry to perform pacing of a target tissue in response to the position and/or the orientation information from the magnetic sensors. The catheter system further includes a display communicatively coupled to the controller circuitry. The controller circuitry is further configured to generate and display a map indicative of positioning of the electrode assembly within a heart. The controller circuitry determines a position of the electrode assembly within an apex portion of the heart based on the signals from the distal electrodes without receiving signals from the spline electrodes. The catheter is configured to perform bipolar pacing of the target tissue during an electrophysiology procedure.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
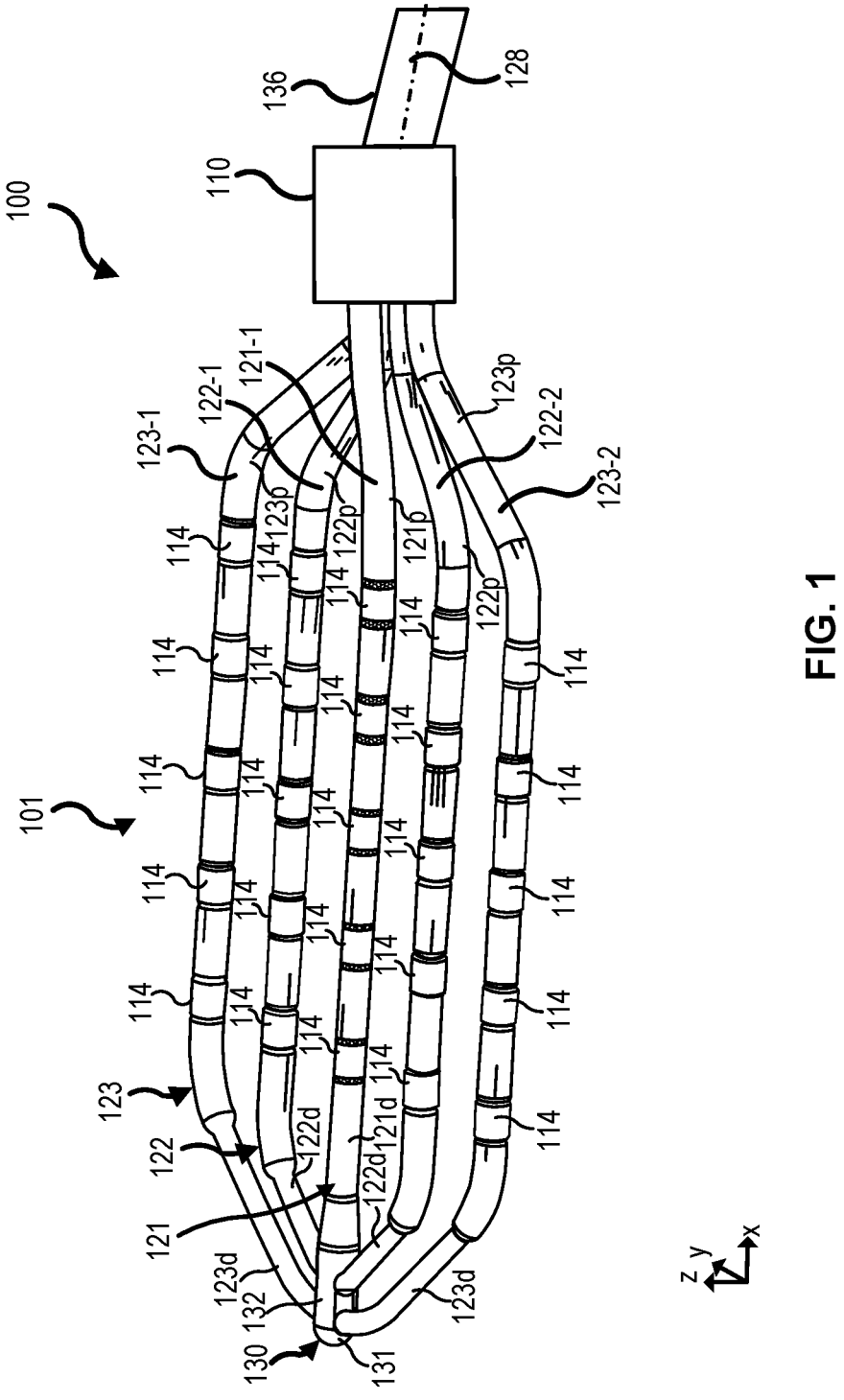
FIG. 1 is an isometric view of an electrode assembly of a high-density electrode catheter, in accordance with various embodiments of the present disclosure.
Figure 2:
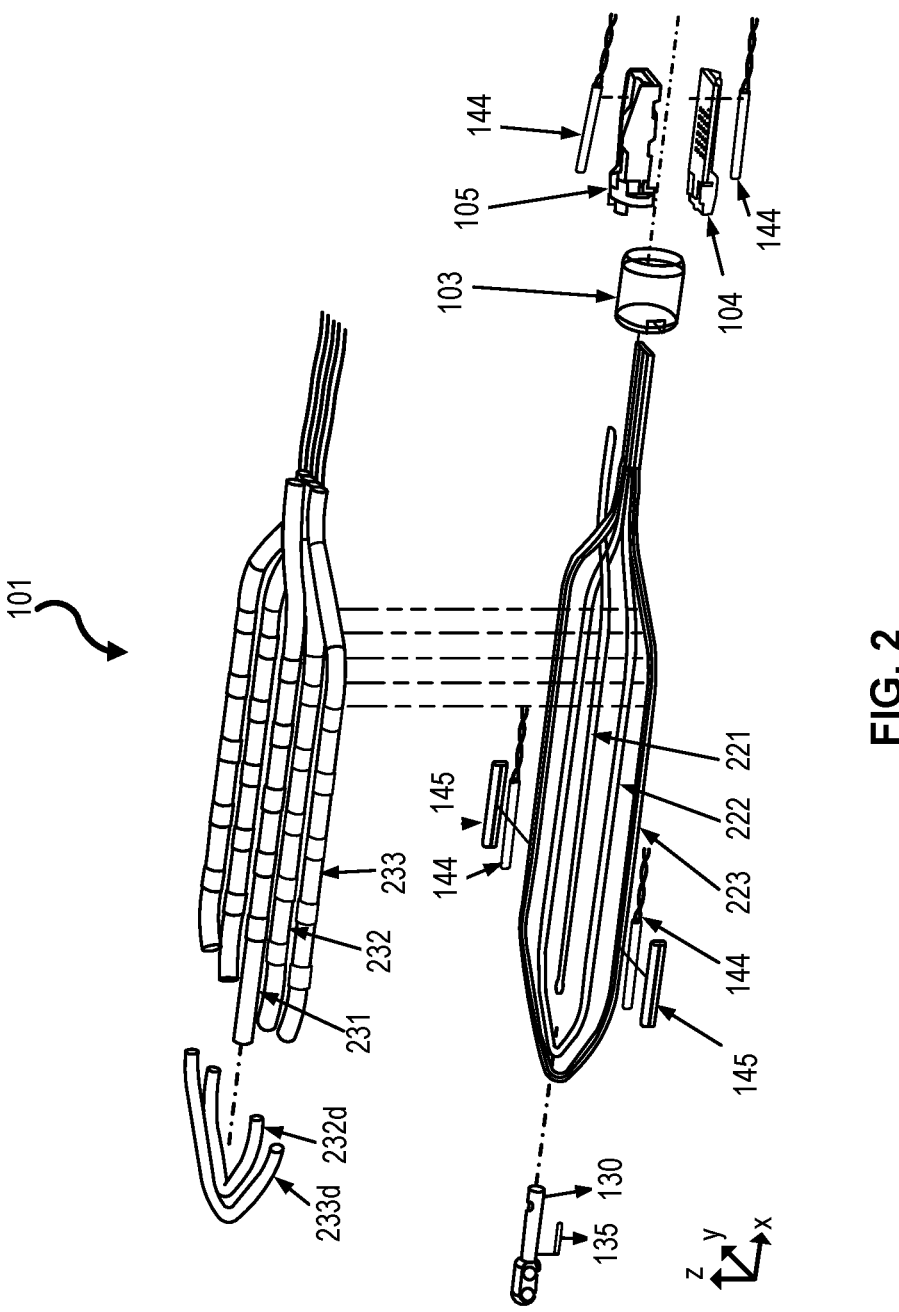
FIG. 2 is an exploded view of the high-density electrode catheter of FIG. 1.

Referring now to the drawings wherein like reference numerals are used to identify identical components in the various views, FIG. 1 is an isometric view of an electrode assembly 101 of a high-density catheter 100, and FIG. 2 is an exploded view of the electrode assembly 101, in accordance with various embodiments of the present disclosure. The electrode assembly 101 includes one or more spline assemblies and a coupler configured to couple distal portions of the spline assemblies. Each spline assembly includes a flexible spline understructure, which may be covered by an insulative cover. A plurality of electrodes can be distributed along a portion of a spline assembly. The spline assembly can be disposed in an expanded or collapsed configuration. In an expanded configuration, as shown in FIG. 1, the spline assemblies are spread out and spaced from each other for form a two-dimensional plane (e.g., x-y plane).

In the examples illustrated herein, the electrode assembly 101 includes at least a first spline assembly 121, a second spline assembly 122, and a distal coupler assembly 130. Alternatively or in addition, the electrode assembly 101 can further include a third spline assembly 123. In the illustrated embodiment, the first spline assembly 121 is disposed approximately at a center of the electrode assembly 101 and the second spline assembly 122 is disposed around the first spline assembly 121. The third spline assembly 123 is disposed on an outer side around the second spline assembly 122. The second spline assembly 122 and the third spline assembly 123 can be configured to expand into U or V shape in the two-dimensional plane (e.g., x-y plane). The distal coupler assembly 130 is configured to receive and secure in place distal portions of the spline assemblies 121-123. In the illustrated example, the spline assemblies 121-123 are spaced from each other and do not cross each other in the two-dimensional plane as well as at the distal coupler assembly 130.

In many embodiments, the first spline assembly 121 includes a single spline 121-1 with a first set of electrodes 114 disposed thereon. The second spline assembly 122 includes a second spline 122-1 with a second set of electrodes 114 disposed thereon and a third spline 122-2 with a third set of electrodes 114 thereon. The spline second assembly 122 has a distal portion 122$d$ and a proximal portion 122$p$. The individual splines 122-1 and 122-2 are connected at the distal portion 122$d$ to form a U-shape. The second set of electrodes 114 are distributed between the proximal portion 122$p$ and the distal portion 122$d$ of the second spline 122-1. The third set of electrodes 114 are distributed between the proximal portion 122$p$ and the distal portion 122$d$ of the third spline 122-2. The second spline 122-1 and the third spline 122-2 are disposed on either side of the first spline 121. Similarly, the third spline assembly 123 includes a fourth spline 123-1 with a fourth set of electrodes 114 disposed thereon, and a fifth spline 123-2 with a fifth set of electrodes disposed thereon. The third spline assembly 123 has a distal portion 123$d$ and a proximal portion 123$p$. The individual splines 123-1 and 123-2 are connected at the distal portion 122$d$ to form a U-shape. The fourth set of electrodes 114 are distributed between the proximal portion 123$p$ and the distal portion 123$d$ of the fourth spline 123-1. The fifth set of electrodes 114 are distributed between the proximal portion 123$p$ and the distal portion 123$d$ of the fifth spline 123-2. As illustrated, the fourth spline 123-1 and the fifth spline 123-2 are disposed on the outer side (away from the first spline assembly 121) of the second spline 122-1 and the third spline 122-2, respectively. In many embodiments, each of the first set of electrodes, the second set of electrodes, the third set of electrodes, the fourth set of electrodes, and the fifth set of electrodes may include 1, 2, 3, 4, 5 or more electrodes. For example, each spline includes 5 electrodes so that the electrode assembly 101 includes a total of 25 spline electrodes.

The spline assemblies 121-123 include understructures, as illustrated in FIG. 2. For example, the first spline assembly 121 includes a first spline understructure 221, the second spline assembly 122 includes a second spline understructure 222, and the third spline assembly 123 includes a third spline understructure 223. The spline understructures 221, 222, and 223 are enclosed in covers 231, 232, and 232, respectively to form the spline assemblies 121, 122, and 123, respectively. In the illustrated embodiment, the electrodes 114 can be supported on the covers 231, 232 and 233 covering the understructures 221, 222, and 223, respectively. Furthermore, distal covers 232$d$ and 233$d$ can be provided to cover the distal portions of the understructures 222 and 223, respectively, thereby forming the distal portions 122$d$ and 123$d$ of the second and third spline assemblies, respectively.

In many embodiments, the distal coupler assembly 130 includes a base member 131 and a distal electrode 132. The base member 131 is configured to receive and accommodate a distal portion of the second spline assembly 122. For example, the base member 131 defines one or more openings to receive and accommodate the distal portion 122$d$ of the second spline assembly 122 and the distal portion 123$d$ of the third spline assembly 123, as illustrated. The distal electrode 132 is configured to be mounted to the base member 131 to secure the distal portion of the second spline understructure within the opening.

Advantageously, the distal coupler assembly 130 facilitates an insertion configuration and a retention configuration. For example, the distal coupler assembly 130 allows insertion and repositioning of the spline assemblies (e.g., 121-123) within openings of the base member 131 to mechanically capture and secure in the spline assemblies in place. Further, the spline assemblies (e.g., 122-123) can be retained by sliding the distal electrode 132 over the base member 131. The distal coupler assembly 130 facilitates the base member 131 and the distal electrode 132 to be made of different materials to provide manufacturing and cost advantages. For example, the base member 131 can be made from lower cost material, such as stainless steel and the distal electrode 132 can be made of a precious metal, such as titanium, platinum, or platinum iridium alloy or even stainless steel. Thus, in addition to mechanical advantages, the distal coupler assembly 130 also allows the distal electrode 132 to be made of a precious metal without incurring the cost of machining the entire coupler from precious metals. The distal electrode 132 is located at the distal most portion of the electrode assembly 101 compared to other electrodes

114. Hence, the distal electrode 132 can advantageously provide signals to determine proximity to a tissue before the electrode assembly 101 is expanded e.g., into a cavity of the heart. In an example, the distal electrode 132 can provide proximity signal to better maneuver the catheter 100 at apex portion of the heart.

Figure 3:
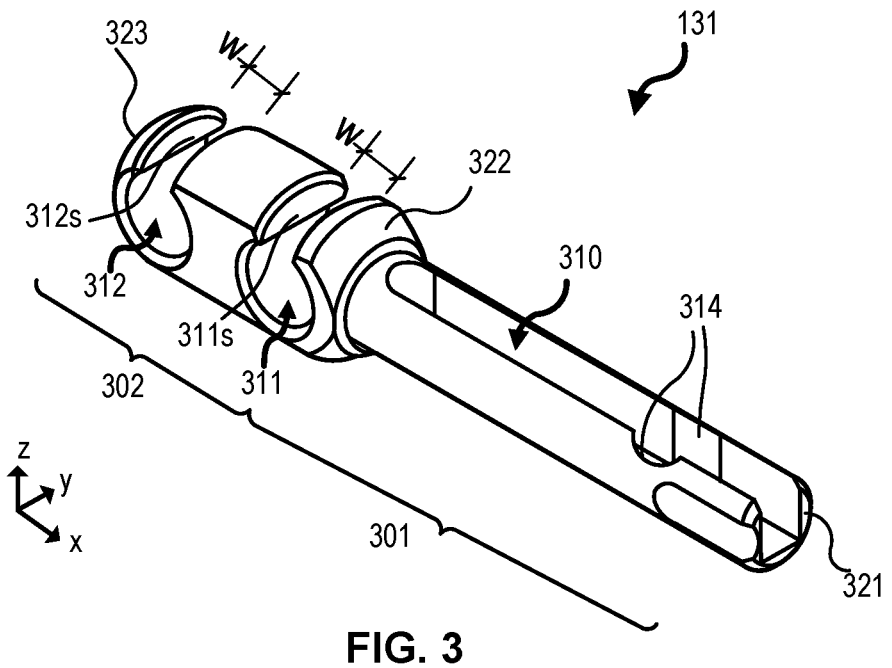
FIG. 3 is an isometric view of a distal coupler of the electrode assembly of FIG. 1.
Figure 4:
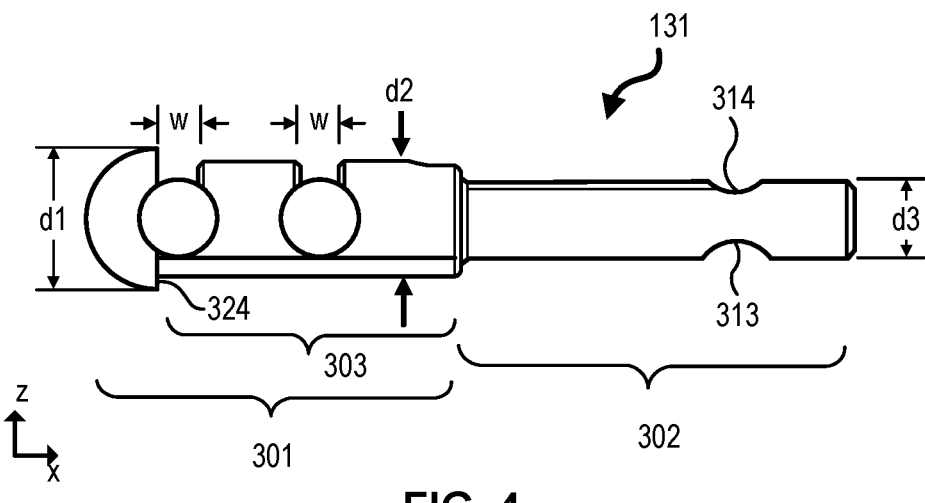
FIG. 4 is a front view of the distal coupler of FIG. 3.

An example construction of the base member 131 of the distal coupler assembly 130 is illustrated in FIG. 3 and FIG. 4. In the illustrated embodiment, the base member 131 includes a proximal shaft portion 301 and a distal shaft portion 302. The proximal shaft portion 301 is configured to receive and secure in place the distal portion 121$d$ of the first spline assembly 121 (in FIG. 1). The distal shaft portion 302 incudes a first opening 311 and a second opening 312 to receive and secure in place the distal portions 122$d$ and 123$d$ of the first spline assembly 122 and the second spline assembly 123, respectively (in FIG. 1). The first opening 311 is proximal to and spaced from the second opening 312 to maintain separation between the spline assemblies 122 and 123 at the distal portions and prevent them from crossing each other.

Figure 8:
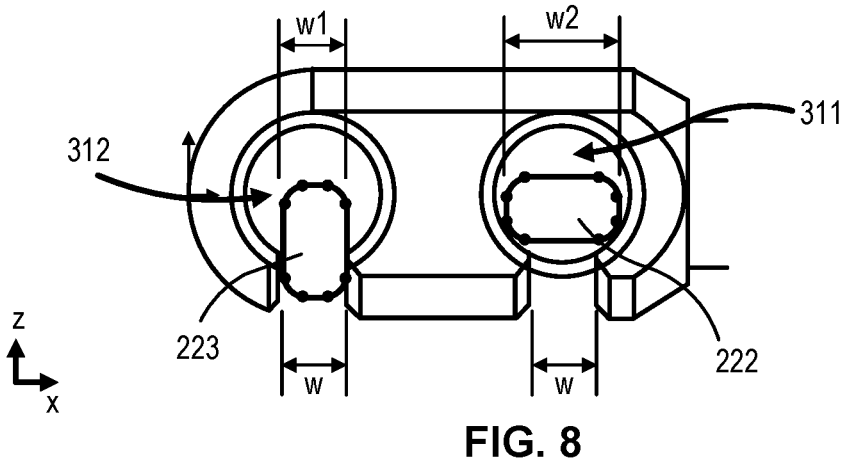
FIG. 8 illustrates the distal coupler of FIG. 4 with a cross-section of a spline understructure of the electrode assembly of FIG. 1 coupled to the distal coupler.

In many embodiments, the openings 311 and 312 include frame slot 311$s$ and 312$s$, respectively. The frame slots are narrow opening leading to a larger cylindrical hole at a center of the base member 131. The frame slots facilitate easy insertion and repositioning of the spline assembly (e.g., 122 and 123) within the openings 311 and 312. As illustrated in FIGS. 3 and 4, the frame slots 311$s$, 312$s$ are circumferential openings having an axially extending width W (e.g., along x-direction) and a transversely extending length (e.g., along the y-direction). The axially extending width W is less than a maximum cross-sectional dimension of a spline understructure (e.g., a dimension W2 of a cross-section of the spline assembly understructures 222, 223, as shown in FIG. 8). The frame slot design allows the frames to "drop" or "clip" into position. Once the understructures are in position, an electrode slides over the proximal end of the coupler covering the slots and securing the spline assemblies in place. Thus, the frame slots advantageously provide ease of assembly of the electrode assembly 101 compared to an opening that may require threaded opening to secure the frames in place, for example.

The frame slots 311$s$, 312$s$ are configured to receive a minimum cross-section dimension of a distal portion (e.g., 122$d$, 123$d$) of the spline understructures (e.g., dimension W1 of a cross-section of the spline assembly understructures 222, 223, as shown in FIG. 8) and deliver the distal portion into the opening such that the distal portion can be rotated to securely position the second spline assembly 122 within the opening. For example, the distal portion 122$d$, 123$d$ of the spline understructures 222, 223 are rotated by approximately 90° within the openings 311 and 312, respectively. Reorienting the spline understructures 222, 223 causes the maximum cross-sectional dimension W2 of the distal portion 222$d$ and 223$d$ to cover the frame slot 311$s$, 312$s$, respectively, and securely install the distal portions 122$d$, 123$d$ in the openings 311, 312 of the base member 131.

It can be understood that the frame slots 311$s$, 312$s$ are provided as examples of the opening 311, 312 without limiting the scope of the present disclosure. Other shapes of the opening are possible. For example, the openings 311, 312 can be a cylindrical hole extending transversely along the distal shaft portion 302 and the frame slots may be omitted.

In many embodiments, the distal shaft portion 302 further includes an electrode receiving portion 303 (see FIG. 4) configured to securely receive the distal electrode 132 between a distal end 323 and a proximal end 322 of the distal shaft portion 302. The electrode receiving portion 303 of the distal shaft portion 302 includes a shoulder 324 (see FIG. 4) at the distal end 323 to prevent axial displacement of the distal electrode 132 upon assembly. The electrode receiving portion 303 of the base member 131 includes a chamfer at the proximal end 322 to slidably receive a distal portion of the cover 231 over the first spline understructure 221 and abut against a proximal end 511 (best shown in FIGS. 7A-7B) of the distal electrode 132 to secure and prevent axial displacement of the distal electrode 132 on the distal shaft portion 302.

As shown in FIG. 4, the distal shaft portion 302 includes a rounded distal end 323 and has a first diameter d1. Advantageously, the rounded distal end 323 can be made of a material (e.g., a soft- or other material) to prevent any trauma or stress to tissue when in contact. The electrode receiving portion 303 has a second diameter d2. The second diameter d2 is smaller than the first diameter d1. The second diameter d2 can be approximately equal to an inner diameter of the distal electrode 132. As such, the distal electrode 132 can be received over the electrode receiving portion 303 and abut against the shoulder 324 to prevent further axial movement toward the distal end 323 of the distal shaft portion 302. Also, once assembled, the inner surface (e.g., 315 in FIG. 5) of the distal electrode 132 closes the slots 311s, 312s and securely holds the distal portions 122d and 123d of the spline assemblies 122 and 123, respectively, within the openings 311, 312.

Figure 5:
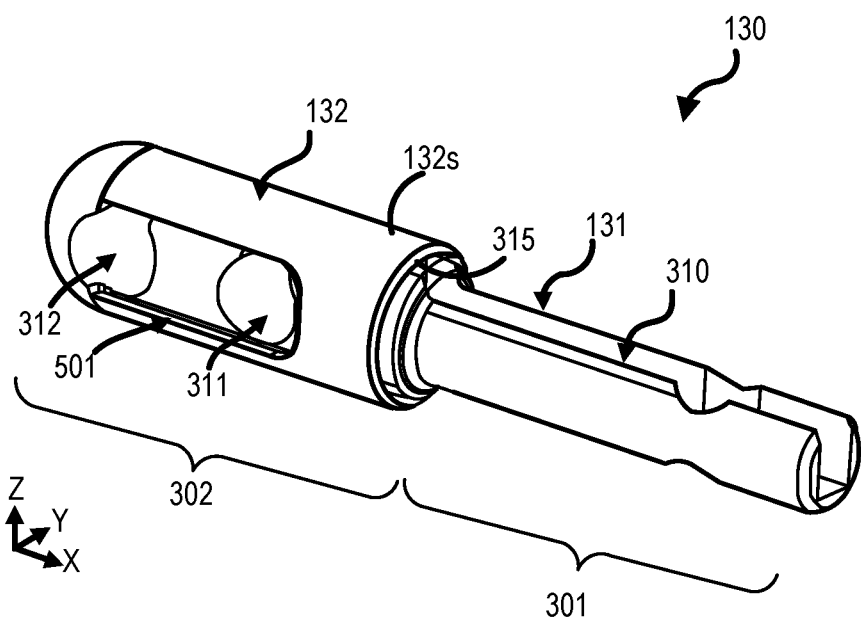
FIG. 5 is an isometric view of a distal coupler assembly of the electrode assembly of FIG. 1.
Figure 6:
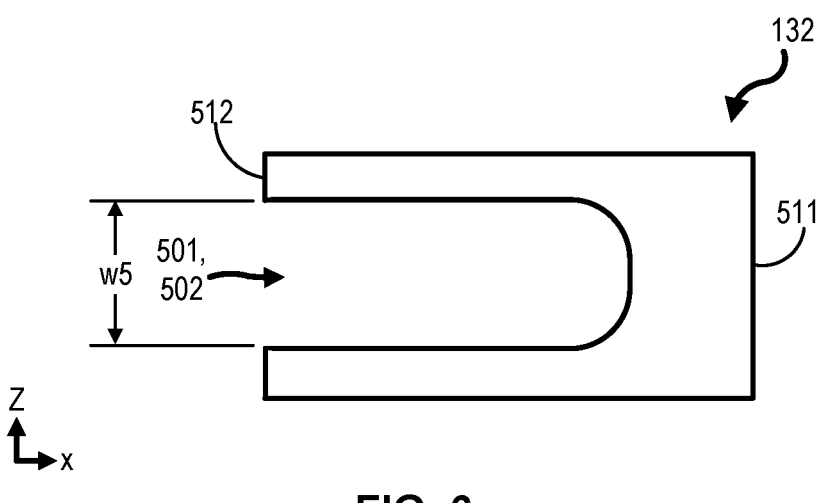
FIG. 6 illustrates a front view of a distal electrode of the distal coupler assembly FIG. 5.

An example construction of the distal electrode 132 of the distal coupler assembly 130 is illustrated in FIG. 5 and FIG. 6. The distal electrode 132 is configured to slidably couple and secure in place with the base member 131. In the illustrated embodiment, the distal electrode 132 is a hollow cylinder including axial slots 501, 502 extending from a distal end 512 toward a proximal end 511. Each of the axial slots 501, 502 has a width W5 and a length corresponding to the openings 311, 312 in the base member 131 to facilitate slidably coupling of the distal electrode 132 to the base member 131 while the distal portions 122d, 123d of the spline assemblies 122, 123 are secured in the openings 311, 312. The distal electrode 132 has a relatively simple construction compared to the base member 131. The distal electrode 132 can be separately manufactured and assembled onto the base member 131. As such, the distal electrode 132 can be manufacture from precious metal within easy machining operations making the distal coupler assembly 130 cost effective while enhancing functionality the electrode assembly 101 due to addition of the distal electrode 132.

Referring to FIGS. 3-5, the proximal shaft portion 301 includes a channel 310 configured to receive the distal portion of the first spline assembly 121. The channel 310 can extend from a proximal end 321 of the proximal shaft portion 301 to the proximal end 322 of the distal shaft portion 302. The first spline understructure 221 includes an enlarged distal end 221e (best seen in FIG. 9 and FIG. 10). The channel 310 includes an enlarged recess 314 sized to receive the enlarged distal end 221e of the first spline understructure 221. This secures and/or prevents relative movement of the first spline understructure 221 with the proximal shaft portion 301 of the base member 131. In some embodiments, the enlarged distal end 221e can be aligned with the enlarged recess 314 and secured in place by adhesive, epoxy, soldering, or other attachment means (e.g., see FIG. 9). Such secure engagement advantageously prevents any relative motion between the frame 221 and the base member 131 during operation. For example, when guiding the high-density catheter through a patient or an introducer to a target location, the catheter may be pulled, pushed, or rotated several times to achieve a desired orientation in the heart of a patient. The securely engaged understructure with the distal coupler can sustain such push, pull, or rotations forces and prevent any undesired movements between components within a small chamber of the heart. The channel 310 further includes a frame access hole 313 (see FIG. 4 and FIG. 10) to access the enlarged distal end 221e of the first spline understructure 221. The frame access hole 313 can advantageously provide attachment means connect an electrical wire to route signals from the distal electrode 132 or sensors disposed in the channel 310.

In many embodiments, the channel 310 extends axially and proximally along the proximal shaft portion 301 and is configured to route a wire (e.g., wire 135 in FIG. 2) from the distal electrode 132 to the first spline understructure 221. The wire can further be accessed at a connector 102 (in FIG. 1 and FIG. 2) and routed to a controller to transmit signals. As an example, the base member 131 provides a wire slot at the end 322 to facilitate receiving and coupling an electrical wire to the distal electrode 132 via welding. For example, the wire slot can be a portion of the channel 310 at the end 322 under an inner surface 315 of the electrode 132. An electrical wire 135 (see FIG. 2) can be coupled to the inner surface 315 of the electrode 132. The distal electrode 132 is made of a conductive material so that an external surface 132s receives signals that can be transmitted via the wire coupled to the inner surface 315. The channel 310 has a depth to receive a sensor to be coupled to the first spline understructure 221 so that the sensor can be concealed within the first spline assembly 121 and the distal coupler assembly 130.

Figures 7A, 7B:
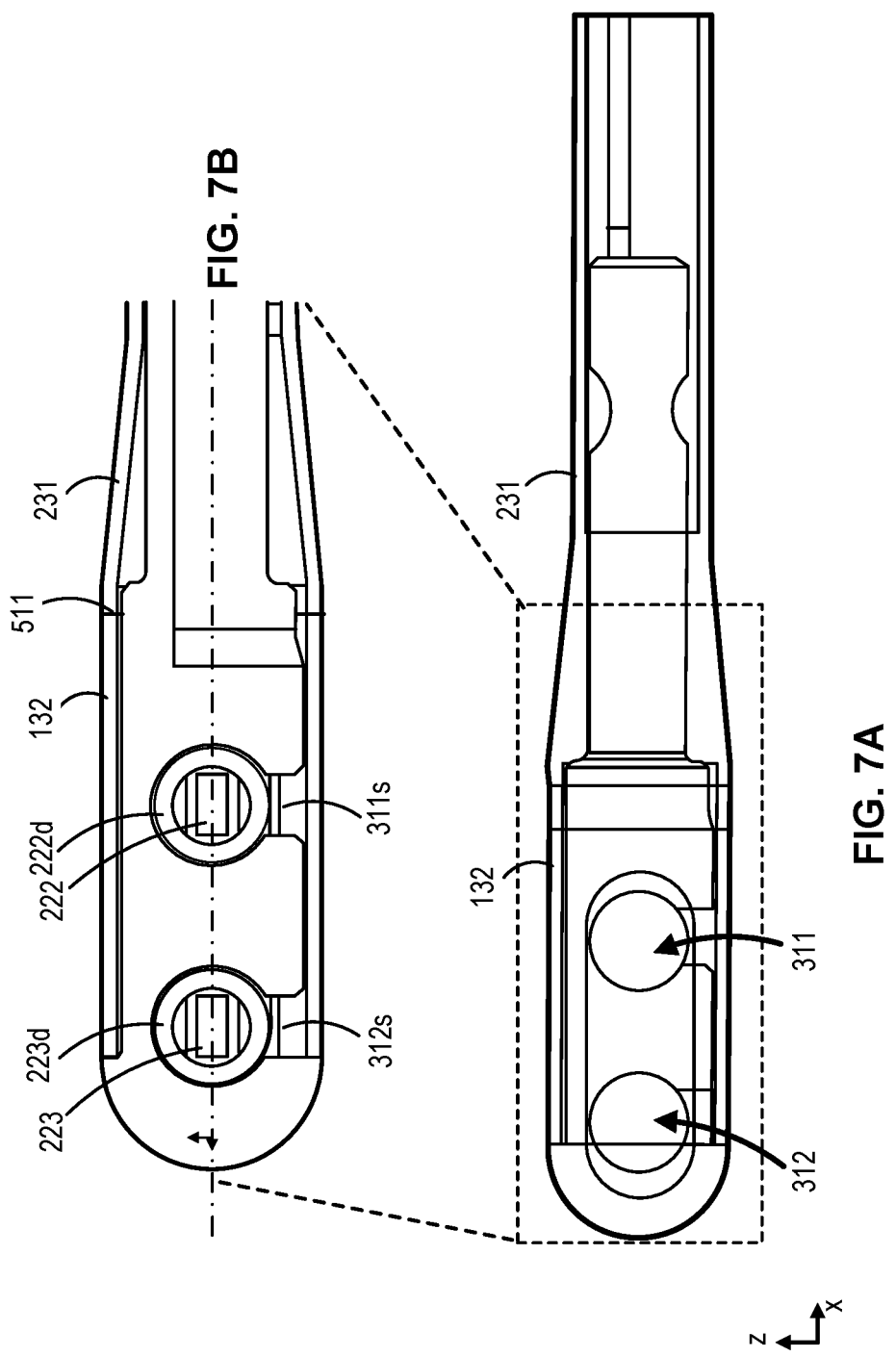
FIG. 7A illustrates a transparent view of the distal coupler assembly of the electrode assembly of FIG. 1.
FIG. 7B is front cross-section view of the distal coupler assembly of the electrode assembly of FIG. 1.

FIG. 7A illustrates a transparent view and FIG. 7B is front cross-section view of the distal coupler assembly 130 of the electrode assembly 101 to further explain assembly of components of the electrode assembly 101 at the distal coupler assembly 130. As illustrated, the base member 131 receives the distal electrode 132, which is further secured by the cover 231. For example, the cover 231 includes an enlarged diameter portion that can slide over the chamfered end 322 (see FIG. 3) and pushes the distal electrode 132 against the shoulder 324 at the distal end 323 thereby securely positioning the distal electrode 132 over the base member 131. Also, as illustrated, the distal portions 222d and 223d of the second spline assembly 122 and the third spline assembly 123 are secured within the openings 311 and 312, respectively. For example, as shown in the FIG. 7B, the second spline understructure 222 is oriented such that its maximum dimension covers the frame slot 311s to secure the second spline assembly 122. Also, even if the second spline understructure 222 is reoriented during operation, the distal electrode 132 ensures the distal portion of the second spline assembly 122 is secured in the opening 311.

Figure 9:
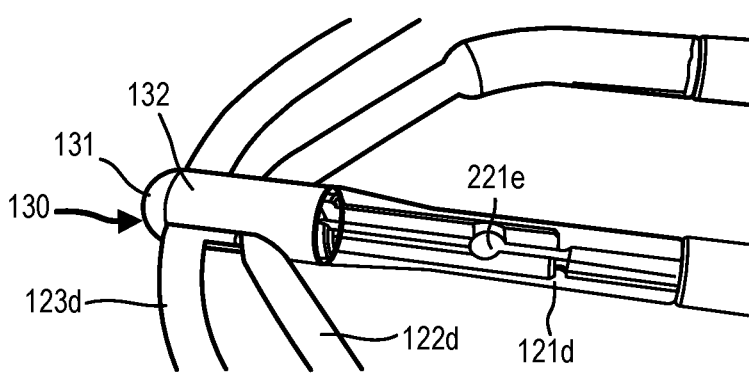
FIG. 9 is top perspective view showing the distal coupler assembly coupled a spline assembly of the electrode assembly of FIG. 1.
Figure 9:
Figure 10:
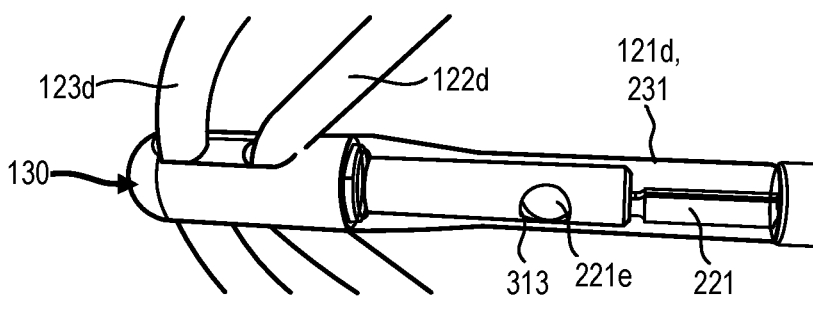
FIG. 10 is bottom perspective view showing the distal coupler assembly coupled a spline assembly of the electrode assembly of FIG. 1.

FIGS. 8, 9 and 10 further illustrate the distal coupler assembly 130 securely coupling the distal portions 122d and 123d of the spline assemblies 122 and 123 within the openings of the distal shaft portion 302 of the base member 131. For example, the third spline assembly 123 can be oriented to dispose the understructure 223 in the opening 312 and reoriented (e.g., by rotating by 90°). The understructure 222 is shown in the reoriented position in the opening 311. Upon coupling the distal portions 122d and 123d, the distal electrode 132 can be slide over the distal portion of the base member 131 by orienting the slots 501, 502 such the distal portions 122d and 123d pass between the slots 501, 503. Furthermore, the distal portion 121*d* of the first spline assembly 121 is securely coupled over the proximal shaft portion 301 of the base member 131. For example, once the distal electrode 132 is in place, the distal portion 121*d* of the first spline assembly is coupled to the proximal shaft portion 301 and the cover 231 can be abutted against the proximal end of the distal electrode 132.

Spline Assemblies and Other Components of HD Catheter

As mentioned earlier, the electrode assembly 101 can include a plurality of spline assemblies configured to form a planar two-dimensional array of electrodes. In many embodiments, the spline assemblies may include two, three, four, five or more number of splines. In the illustrated embodiments, e.g., FIGS. 1 and 2, five spline configuration of the electrode assembly is discussed as an example. Each spline can include a linear sequence of electrodes 114 of the assembly 101 together forming the planar two-dimensional array of electrodes. The spline assembly configuration is further discussed in detail as follows. Additionally, examples of high-density catheters with a planar two-dimensional array of electrodes are discussed in U.S. Patent Publication No. 2022/0054198, which is incorporated herein by reference in its entirety.

The first spline assembly 121 includes the single spline 121-1, which is aligned with a central longitudinal axis 128 of the high-density catheter 100. An electrode support portion is between the proximal portion (e.g., 121*p*, 122*p*, and 123*p*) and the distal portion (e.g., 121*d*, 122*d*, and 123*d*) to support the electrodes 114. The electrode support portion has a straight-line configuration in an undeformed state (e.g., when not being flexed to conform to a tissue surface). Each of the second spline distal portion 122*d* and the third spline distal portion 123*d* extends through the distal coupler assembly 130 and can move through the distal couple assembly 130 during reconfiguration of the electrode assembly 101, such as, for example, during flexing of the electrode assembly 101 to conform the electrode assembly 101 with a tissue surface to interface the electrodes 114 with the tissue surface and during reconfiguration of the electrode assembly 101 between a collapsed configuration and an expanded configuration (shown in FIG. 1). In the expanded configuration shown in FIG. 1, each of the electrode portions of the spline assemblies 122-123 is offset from and parallel to the first electrode portion of the first spline assembly 121. The electrode assembly 101, however, can be configured so that each of the electrode portions of the spline assemblies 122-123 is offset from and oriented non-parallel to the first electrode portion of the first spline assembly 121. Moreover, although the electrodes 114 are distributed in a regular two-dimensional grid pattern in the illustrated embodiment, the electrodes 114 can be distributed in any suitable arrangement in which the electrodes 114 have suitable offsets from each other including, but not limited to, non-orthogonal distribution patterns in which the electrodes on adjacent electrode portions are offset longitudinally along the axis 128.

Each of the first spline assembly 121, the second spline assembly 122, and the third spline assembly 123 is configured to have a suitable flexural flexibility so that the electrode assembly 101 can be conformed to a target tissue surface for any suitable medical purpose such as, but not limited to, to measure electrical activity of the heart via the electrodes 114, to perform a medical treatment using the electrodes 114, and/or to generate a surface model of the target tissue surface. In the illustrated embodiment, each of electrode portions has five of the electrodes 114 but can have any suitable alternate number of the electrodes 114 (e.g., 1, 2, 3, 4, 6, 7, 8, or more). The electrodes 114 are spaced apart on the electrode assembly 101 to form a two-dimensional distribution of the electrodes 114.

The electrodes 114 can be configured for use in diagnostic, therapeutic, and/or mapping procedures. For example and without limitation, the electrodes 114 can be configured for use in electrophysiological studies, pacing, cardiac mapping, and/or ablation. In some embodiments, the electrodes 114 can be configured for use in performing unipolar or bipolar ablation, which can be used to create specific lines or patterns of lesions. In some embodiments, the electrodes 114 can receive electrical signals from the heart, which can be used for electrophysiological studies. In some embodiments, the electrodes 114 can perform a location or position sensing function related to cardiac mapping. As another example, the distal electrode 132 of the distal coupler assembly 130 and a spline electrode 114 of a spline assembly (e.g., a center spline assembly 121, an inner spline assembly 122, or an outer spline assembly 123) can be configured to transmit coordinated electrical signals to effect bipolar pacing, discussed in further detail later in the disclosure. Alternatively or additionally, the distal electrode 132 of the distal coupler assembly 130 and a shaft electrode (not illustrated) on the proximal shaft section of the catheter can be configured to transmit coordinated electrical signals to effect bipolar pacing.

In many embodiments, the high-density catheter 100 includes a catheter shaft 136 (see also FIG. 1). The catheter shaft 136 includes a proximal end and a distal end. The distal end of the catheter shaft 136 can be attached to the connector 102 (see FIG. 1). Referring to FIG. 2, the connector 102 can include frame locking members 104 and 105 configured to receive proximal portions of understructure of the splines 121-1, 122-1, 122-2, 123-1, and 122-2. The frame locking members 104 and 105 can be covered by a connector cover 103. The catheter shaft 136 can be made to have a suitable flexural compliance so that it can be advanced through suitable paths through a patient's vasculature. In some embodiments, the catheter shaft 136 includes one or more ring electrodes disposed along a length of the catheter shaft 136. The ring electrodes can be configured for use in diagnostic, therapeutic, and/or mapping procedures.

The high-density catheter 100 can further include any additional suitable components. For example, the high-density catheter 100 can further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

In many embodiments, each of the first spline assembly 121, the second spline assembly 122, and the third spline assembly 123 includes a flexible understructure member as shown in FIG. 2. The respective flexible understructure members can be formed from any suitable elastically deformable material (e.g., Nitinol). Each of the understructures 221-223 of the spline assemblies 121-123 has a rectangular cross-section with a width and a height that is less than the width to bias the flexibility of the electrode assembly 101 to enhance the conformability of the electrode assembly 101 with a tissue surface.

In the illustrated embodiment, in FIGS. 1 and 2, each of the proximal portions, the electrode portions, of the understructure members 221, 222, 223 is enclosed within a non-conductive shell or cover 231, 232, and 233. Also, the distal portions of the understructures 222 and 223 are enclosed within the non-conductive shell or cover 232*d* and 233*d*, respectively. The non-conductive shell can include a tube that defines a longitudinally extending lumen in which the respective understructure member is disposed. The non-conductive shell can be formed from any suitable non-conductive material, such as a suitable polymer material.

Among other things, the electrode assembly 101 can be configured for use to: (1) define regional propagation maps for tissue surface areas (e.g., one centimeter square areas) of an interior atrial wall of the heart; (2) identify complex fractionated atrial electrograms for ablation; (3) identify localized, focal potentials between the electrodes for higher electrogram resolution; and/or (4) more precisely target areas for ablation. In many embodiments, the electrode assembly 101 is configured to be conformable to, and remain in contact with, cardiac tissue even in the presence of erratic cardiac motion, thereby avoiding mapping error(s) and/or ablation problems that can occur as a result of intermittent tissue-electrode contact.

Additionally, the electrode assembly 101 may be useful for epicardial and/or endocardial use. For example, the electrode assembly 101 may be used in an epicardial procedure where the electrode assembly 101 is positioned between the myocardial surface and the pericardium. Alternatively, the electrode assembly 101 may be used in an endocardial procedure to quickly sweep and/or analyze the inner surfaces of the myocardium and quickly create high-density maps of the heart tissue's electrical properties.

In many embodiments, the electrode assembly 101 includes one or more location sensors 144, such as an electromagnetic location sensor. For example, as illustrated in FIG. 2, the distal portion 121*d* of the first spline assembly 121 can house a location sensor 144 within the channel 310 (see FIG. 3) of the distal electrode coupler 130. One or more location sensors 144 can be disposed within any suitable portion of the first spline assembly 121 including, but not limited to, distal to the electrodes 114, in between any two of the electrodes 114, and/or proximal to the electrodes 114. The position and orientation of the location sensor(s) 144 within a patient's body can be determined as discussed herein. In a similar manner, one or more location sensors 144 can be disposed within any suitable portion of the second spline assembly 122 and/or within any suitable portion of the third spline assembly 123, within the connector 102, and/or within the catheter shaft 136. In many embodiments, the high-density catheter 100 includes one or more locations sensors 144 in the catheter shaft 136 for determining and tracking positions and orientations of the catheter shaft 136. In many embodiments, the location sensor(s) 144 is configured to sense a position and orientation of the location sensor(s) 144 with five degrees of freedom (5 DOF). In many embodiments, two location sensors 144 are used to sense a position and orientation of the high-density catheter 100 to six degrees of freedom (6 DOF). As discussed herein, the location sensor(s) 144 can be disposed in a magnetic field and produce one or more signals indicative of the position and orientation of the location sensor(s) 144. The location sensor(s) 144 may attached to the understructure 221, 222, and/or 223 by enclosing the sensor in a tube 145 and attaching the tube 145 to the understructure 221, 222, and/or 223 at a desired location (see FIG. 2). The present disclosure is not limited to a particular location of the location sensor 144. The location sensor 144 can be located within the spline assembly (also referred as paddle), a shaft coupled to the spline assembly, or other locations of the electrode assembly.

Figure 11:
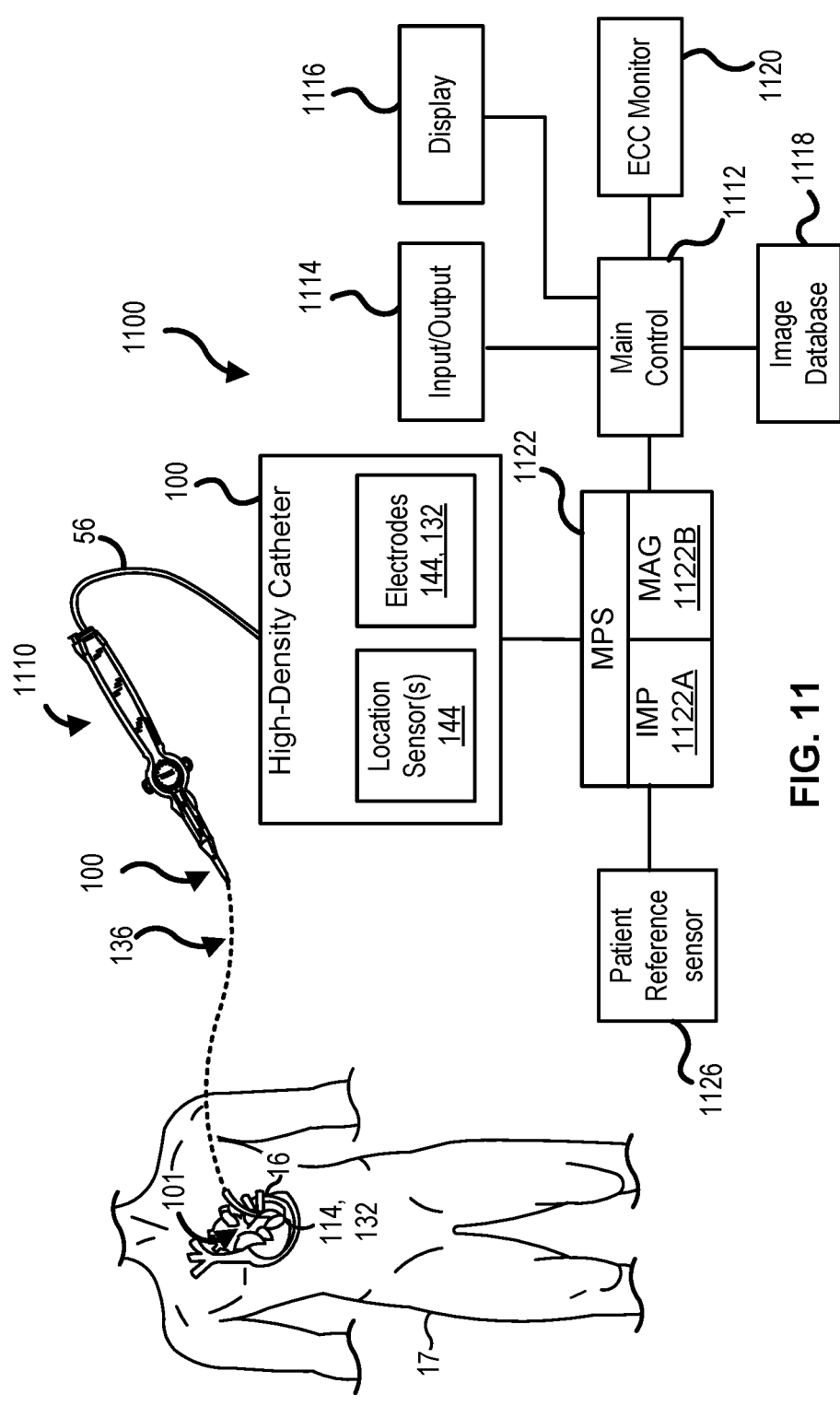
FIG. 11 illustrates an example medical device localization system that can be employed in conjunction with the electrode assembly, in accordance with embodiments of the present disclosure.

As shown in FIG. 11, the electrode assembly 101 is configured to be conformable to a tissue (e.g., cardiac tissue)

to interface the electrodes 114 with the tissue. In many embodiments, the electrode assembly 101 has a suitable flexibility to accommodate suitable flexure of the electrode assembly 101 in response to suitable interface forces between the electrode assembly 101 and the tissue.

The configuration of the electrode assembly 101 discussed herein facilitates insertion of the electrode assembly 101 using a handle 1110 of the catheter, deployment of the electrode assembly 101 within the heart 16, and withdrawal of the electrode assembly 101 from the patient by accommodating relative movement between the first spline assembly 121, the second spline assembly 122, and the third spline assembly 123, which can serve to avoid inducing high localized strains in the electrode assembly 101 that may result absent the relative movement accommodation. For example, upon entering a target chamber of the heart 16, the electrodes 114 of the spline assemblies 121-123 and the distal electrode 132 of the distal coupler assembly can expanded, collapsed, advanced, or retracted to receive signals. The signals can be transmitted via the connector 56 to a system for analyzing the signal e.g., to determine localization. In some embodiments, the electrode assembly 101 can be inserted within the heart 16 through an introducer or a delivery catheter.

Localization Systems

The high-density catheter 100 can be used in conjunction with any suitable medical device localization system, such as those referenced and/or described herein. For example, the high-density catheter 100 can be used in conjunction with the catheter localization systems and methods described in U.S. Patent Publication No. 2020/0138334 A1 entitled "Method for Medical Device Localization based on Magnetic and Impedance Sensors", the entire disclosure of which is incorporated herein by reference.

FIG. 11 also illustrates a diagrammatic view of a medical device localization system 1100 that can be used in conjunction with the high-density catheter 100. The system 1100 includes a main electronic control unit 1112 (e.g., a processor) having various input/output mechanisms 1114, a display 1116, an optional image database 1118, an electrocardiogram (ECG) monitor 1120, a localization system, such as a medical positioning system 1122, and the high-density catheter 100. As described herein, in some embodiments the high-density catheter 100 includes the electrodes 114, 132 and one or more of the location sensors 144 (which are in some embodiments configured as magnetic location sensors).

The input/output mechanisms 1114 may include conventional apparatus for interfacing with a computer-based control unit including, for example, one or more of a keyboard, a mouse, a tablet, a foot pedal, a switch and/or the like. The display 1116 may also comprise conventional apparatus, such as a computer monitor.

Various embodiments described herein may find use in navigation applications that use real-time and/or pre-acquired images of a region of interest. Therefore, the system 1100 may optionally include the image database 1118 to store image information relating to the patient's body. Image information may include, for example, a region of interest surrounding a destination site for the high-density catheter 100 and/or multiple regions of interest along a navigation path contemplated to be traversed by the high-density catheter 100. The data in the image database 1118 may include known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database 1118 acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from the ECG monitor 1120. It should be understood that the foregoing embodiments are examples only and not limiting in nature. For example, the image database 1118 may also include three-dimensional image data as well. It should be further understood that the images may be acquired through any imaging modality, now known or hereafter developed, for example X-ray, ultra-sound, computerized tomography, nuclear magnetic resonance or the like.

The ECG monitor 1120 is configured to continuously detect an electrical timing signal of the heart organ through the use of a plurality of ECG electrodes (not shown), which may be externally affixed to the outside of a patient's body. The timing signal generally corresponds to a particular phase of the cardiac cycle, among other things. Generally, the ECG signal(s) may be used by the control unit 1112 for ECG synchronized play-back of a previously captured sequence of images (cine loop) stored in the database 1118. The ECG monitor 1120 and ECG-electrodes may both include conventional components.

Another medical positioning system sensor, namely, a patient reference sensor (PRS) 1126 (if provided in the system 1100) can be configured to provide a positional reference of the patient's body so as to allow motion compensation for patient body movements, such as respiration-induced movements. Such motion compensation is described in greater detail in U.S. Pat. No. 10,069,668, entitled "Compensation of Motion in a Moving Organ Using an Internal Position Reference Sensor", hereby incorporated by reference in its entirety as though fully set forth herein. The PRS 1126 may be attached to the patient's manubrium sternum or other location. The PRS 1126 can be configured to detect one or more characteristics of the magnetic field in which it is disposed, wherein medical positioning system 1122 determines a location reading (e.g., a P&O reading) indicative of the PRS's position and orientation in the magnetic reference coordinate system.

The medical positioning system 1122 is configured to serve as the localization system and therefore to determine position (localization) data with respect to the one or more location sensors 144 and/or the electrodes 114, 132 and output a respective location reading. In an embodiment, the medical positioning system 1122 may include a first medical positioning system or an electrical impedance-based medical positioning system 1122A that determines locations of the electrodes 114, 132 in a first coordinate system, and a second medical positioning system or magnetic field-based medical positioning system 1122B that determines location(s) of the location sensor(s) 144 in a second coordinate system. In an embodiment, the location readings may each include at least one or both of a position and an orientation (P&O) relative to a reference coordinate system (e.g., magnetic based coordinate system or impedance-based coordinate system). For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of the location sensor(s) 144 in a magnetic field relative to a magnetic field generator(s) or transmitter(s) and/or the electrodes 114, 132 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

The impedance based medical positioning system 1122A determines locations of the electrodes 114, 132 based on capturing and processing signals received from the electrodes 114, 132 and external electrode patches while the electrodes 114, 132 are disposed in a controlled electrical field (e.g., potential field) generated by the electrode patches, for example. FIG. 11 also illustrates a diagrammatic overview of an exemplary embodiment of the electrical impedance-based medical positioning system ('MPS system') 1122A. The MPS system 1122A may include various visualization, mapping and navigation components as known in the art, including, for example, an EnSite™ X EP System commercially available from Abbott Laboratories or as seen generally by reference to U.S. Pat. No. 7,263,397 entitled "Method and Apparatus for Catheter Navigation and Location and Mapping in the Heart" to Hauck et al., or U.S. Pat. No. 7,885,707 to Hauck entitled "Method of Scaling Navigation Signals to Account for Impedance Drift in Tissue", both owned by the common assignee of the present invention, and both hereby incorporated by reference in their entireties.

The magnetic-based medical positioning system 1122B determines locations (e.g., P&O) of the location sensor(s) 144 in a magnetic coordinate system based on capturing and processing signals received from the location sensor(s) 144 while the location sensor 144 is disposed in a controlled low-strength alternating current (AC) magnetic (e.g., magnetic) field. Each location sensor 144 and the like may include a coil and, from an electromagnetic perspective, the changing or AC magnetic field may induce a current in the coil(s) when the coil(s) are in the magnetic field. The location sensor(s) 144 is thus configured to detect one or more characteristics (e.g., flux) of the magnetic field(s) in which it is disposed and generate a signal indicative of those characteristics, which is further processed by medical positioning system 1122B to obtain a respective P&O for the location sensor(s) 144 relative to, for example, a magnetic field generator.

It should be understood that the high-density catheter 100 may be used for any other suitable diagnostic and/or therapeutic purposes. Accordingly, the high-density catheter 100 can be configured to perform ablation procedures, cardiac mapping, electrophysiological (EP) studies and other diagnostic and/or therapeutic procedures. Embodiments are not limited to any one type of catheter or catheter-based system or procedure.

Applications

The high-density catheter 100 can be used in conjunction with any suitable catheter system, such as those referenced and/or described herein. For example, the high-density catheter 100 can be used to generate an electrophysiological map of electrical activity within a patient's heart to diagnose cardiac arrythmias. The high-density catheter 100 can be used to selectively alter the patient's heart tissue to reduce or eliminate the pathological electrical condition to reduce or eliminate occurrence of the cardiac arrythmia. The high-density catheter 100 can configured for use in performing any suitable treatment, such as, but not limited to, radio frequency (RF) ablation, pulsed field ablation (PFA), cryoablation, laser ablation, chemical ablation, high-intensity focused ultrasound ablation, microwave ablation, and/or other ablation treatments.

For example, and in some embodiments, the high-density catheter 100 may be configured as a bipolar electrode assembly for use in bipolar-based electroporation therapy. Specifically, the electrodes 114, 132 of the high-density catheter 100 can be individually electrically coupled to an electroporation generator (e.g., via suitable electrical wire or other suitable electrical conductors extending through the catheter shaft 136) and are configured to be selectively energized by the electroporation generator with opposite polarities to generate a potential and corresponding electric field therebetween, for PFA therapy. That is, one of electrodes 114, 132 can be configured to function as a cathode, and another of the electrodes 114, 132 can be configured to function as an anode. Any suitable combination of the electrodes 114 of the electrode assembly 101 can be used as anodes and cathodes. For example, all the electrodes 114 on one of the electrode portions can be employed as a cathode and all the electrodes 114 on an adjacent one of the electrode portions can be employed as an anode. As another example, every other of the electrodes 114 along one of the electrode portions can be employed as a cathode and the other of the electrodes 114 along the electrode portion can be employed as an anode. The electrodes 114, 132 may be any suitable electroporation electrodes. In the exemplary embodiment, the electrodes 114 are ring electrodes. The electrodes 114, 132, may have any other suitable shape or configuration. The shape, size, and/or configuration of the electrodes 114, 132 may impact various parameters of the applied electroporation therapy. For example, increasing the surface area of one or both of the electrodes 114, 132 may reduce the applied voltage needed to cause the same level of tissue destruction. Moreover, although each of the electrodes 114, 132 is illustrated as a single electrode, either or both of the electrodes 114 and the distal electrode 132 may be alternatively embodied as two or more discrete electrodes.

Ablation therapy may be used to treat various conditions afflicting the human anatomy. One such condition in which ablation therapy may be used is the treatment of cardiac arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter) . Arrhythmias can create a variety of dangerous conditions including loss of synchronous atrioventricular contractions and stasis of blood flow. It is believed that the primary cause of atrial arrhythmia is stray electrical signals within the left or right atrium of the heart. The ablation catheter imparts ablative energy (e.g., radiofrequency energy, PFA, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

Electroporation is a non-thermal ablation technique that involves applying strong electric fields that induce pore formation in the cellular membrane. The electric field may be induced by applying a relatively short duration pulse which may last, for example, from a nanosecond to several milliseconds. Such a pulse may be repeated to form a pulse train. When such an electric field is applied to tissue in an in vivo setting, the cells in the tissue are subjected to a trans-membrane potential, which opens the pores on the cell wall. Electroporation may be reversible (i.e., the temporally opened pores will reseal) or irreversible (i.e., the pores will remain open), causing cellular destruction. For example, in the field of gene therapy, reversible electroporation is used to transfect high molecular weight therapeutic vectors into the cells. In other therapeutic applications, a suitably configured pulse train alone may be used to cause cell destruction, for instance by causing irreversible electroporation.

In some embodiments, the high-density catheter 100 is used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field (i.e., pulsed field ablation (PFA)) in the form of short-duration pulses (e.g., 0.1 to 20 ms duration) between closely spaced electrodes capable of delivering an electric field strength of about 0.1 to 1.0 kV/cm.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

Figure 12:
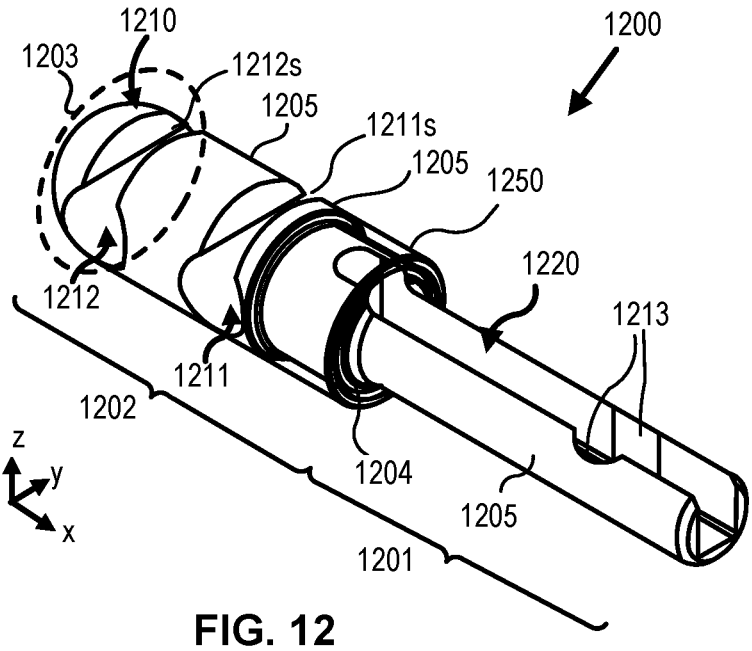
FIG. 12 illustrates another example of a distal coupler of an electrode assembly, in accordance with embodiments of the present disclosure.
Figure 13:
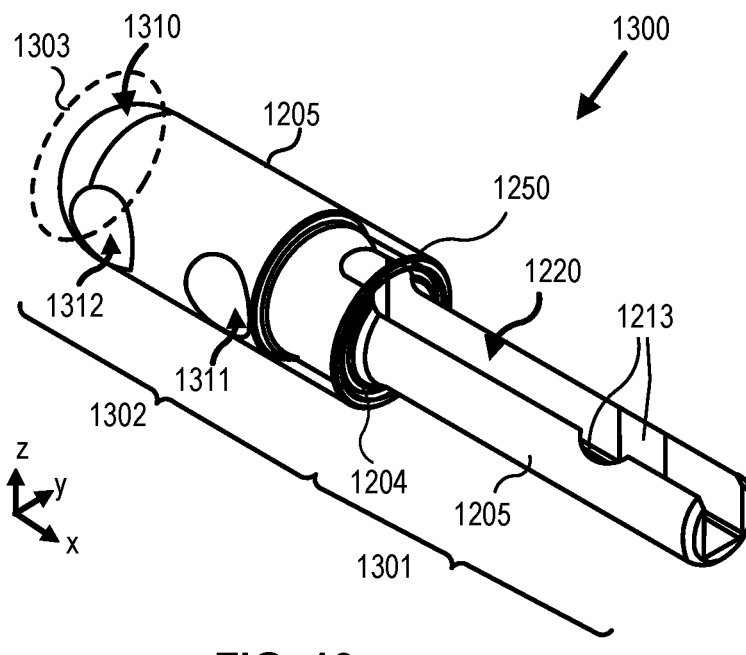
FIG. 13 illustrates yet another example of a distal coupler of an electrode assembly, in accordance with embodiments of the present disclosure.

FIG. 12 and FIG. 13 illustrate examples of a distal coupler of an electrode assembly, in accordance with embodiments of the present disclosure. FIG. 12 shows a distal coupler 1200 with frame slots to receive distal portions of splines of an electrode assembly, according to embodiments discussed herein. FIG. 13 shows a distal coupler 1300 with cylindrical holes or channels to receive distal portions of splines of an electrode assembly, according to embodiments discussed herein. These couplers 1200, 1300 can have similar construction as the distal coupler 130 discussed herein, as such some of the details (e.g., related to base member) may be omitted for brevity. In illustrated embodiments, the distal couplers 1200, 1300 can be further configured to provide electrical isolation (e.g., via insulation coating) between different portions of the respective distal couplers 1200, 1300. In one embodiment, the distal electrodes 1200, 1300 can be a single piece component e.g., manufactured from an electrically conductive material with one or more portions being electrically isolated (e.g., via an insulation coating) from each other. For example, a first portion may be a tip portion and a second portion may be a proximal portion serving as a distal electrode. The distal couplers 1200, 1300 may have a unitary construction where a distal electrode may be integrally formed with a base member. In illustrated embodiments, the base member can be electrically isolated from the distal electrode, as further discussed below.

Referring to FIG. 12, the distal coupler 1200 has a similar construction as the distal coupler 130. For example, the distal coupler 1200 includes a base member 1210 and a distal electrode 1250. The base member 1210 includes a proximal portion 1201 and a distal portion 1202. The distal portion 1202 includes openings 1211, 1212 with frame slots 1211s, 1212s to receive distal portions of splines of an electrode assembly (e.g., portions 122d, 123d of the electrode assembly 101 in FIG. 1). The proximal portion 1201 further includes a channel 1220 configured to receive the distal portion of a spline assembly (e.g., portion 121*d* of the spline 121 in FIG. 1). The channel 1220 further includes an enlarged recess 1213 to access an enlarged distal end (e.g., 221*e* of the first spline understructure 221 in FIG. 2). The enlarged recess 1213 can advantageously provide attachment means to electrically connect with the base member 1210.

In many embodiments, the base member 1210 and the distal electrode 1250 are made of electrically conductive material. Furthermore, the base member 1210 and the distal electrode 1250 are electrically isolated from each other. In some embodiments, one or more portions of the base member 1210 can be coated with an insulation material to electrically isolate the base member 1210 from the distal electrode 1250. For example, a circumferential portion 1205 can be coated with an electrically insulating material, while a tip portion 1203 can remain uncoated. Additionally or alternatively, inner surfaces of the openings 1211, 1212 may be uncoated. The uncoated tip portion 1203 can receive electrical signals upon contacting a target tissue. The tip portion 1203 can further transmit the electrical signals to the proximal portion 1201 and further to a spline understructure (e.g., the understructure of the spline 121 in FIG. 1).

The distal electrode 1250 can be coupled to a proximal portion 1201 of the base member 1210. For example, the proximal portion 1201 includes a step portion 1204 on which the distal electrode 1250 is disposed. The distal electrode 1250 is a hollow cylinder separately manufactured and tightly fitted over the step portion 1204 of the base member 1210. The distal electrode 1250 has an external diameter equal to the diameter of the base member 1210. The distal electrode 1250 can transmit electrical signals upon contact with the target tissue.

As the distal electrode 1250 and the base member 1210 are electrically isolated, the electrical signals transmitted by the distal electrode 1250 and the tip portion 1203 are also isolated from each other. Thus, a first signal may be transmitted via the tip portion 1203 and a second signal may be transmitted via the distal electrode 1250. In some embodiments, such a configuration facilitates bipolar pacing via the tip portion 1203 and the distal electrode 1250. For example, the tip portion 1203 and the distal electrodes 1250 are axially spaced from each other as such an electrical potential can be applied therebetween to facilitate bipolar pacing. In some embodiments, such bipolar pacing may be performed during diagnosis, mapping of electrical signals, during ablation, or post-ablation. In some embodiments, the distal electrode 1250, 1350 in combination with one of the spline electrodes (e.g., 114 in FIG. 1) can also be used to perform pacing.

Referring to FIG. 13, the distal coupler 1300 has a similar construction as the distal couplers 1200 and 130. Similar elements are given the same reference numbers for brevity of description. For example, the distal coupler 1300 includes a base member 1310 and a distal electrode 1250. The base member 1310 includes a proximal portion 1301 and a distal portion 1302. The distal portion 1302 includes openings 1311, 1312 in the form of cylindrical holes instead of frame slots (e.g., 1211*s* and 1212*s* in the coupler 1200) to receive distal portions of splines of an electrode assembly (e.g., portions 122*d*, 123*d* of the electrode assembly 101 in FIG. 1). As discussed herein, the base member 1310 and the distal electrode 1250 are made of electrically conductive material, while being electrically isolated from each other. In some embodiments, one or more portions (e.g., illustrated by 1205) of the base member 1310 can be coated with an insulation material to electrically isolate the base member 1310 from the distal electrode 1250. For example, a circumferential portion 1205 can be coated with an electrically insulating material, while a tip portion 1303 can remain uncoated. Additionally or alternatively, inner surfaces of the openings 1311, 1312 may be uncoated. The uncoated tip portion 1303 can receive electrical signals upon contacting a target tissue. The tip portion 1303 can further transmit the electrical signals via the uncoated portions of the opening 1311, 1312 to the proximal portion 1301 and further to a spline understructure (e.g., the understructure of the spline 121 in FIG. 1).

The proximal portion 1301 is similar to the proximal portion of 1201, which includes the channel 1220 configured to receive a distal portion of a spline assembly (e.g., portion 121*d* of the spline 121 in FIG. 1). The channel 1220 further includes the enlarged recess 1213 to insert an enlarged distal end (e.g., 221*e* of the first spline understructure 221 in FIG. 2). The enlarged recess 1213 can advantageously provide attachment means to electrically connect the base member 1310 so that electrical signals from the tip portion 1303 can be routed through an electrical assembly.

Figure 14:
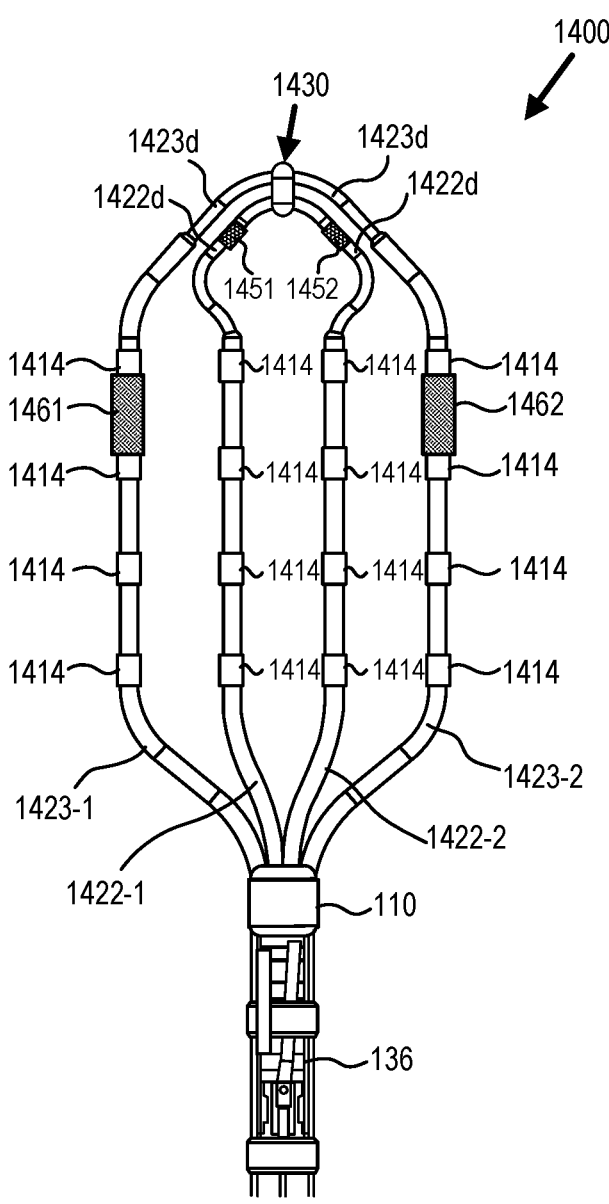
FIG. 14 illustrates a four-spline configuration of an electrode assembly, where distal electrodes are disposed at distal portions of inner splines, in accordance with embodiments of the present disclosure.
Figure 15:
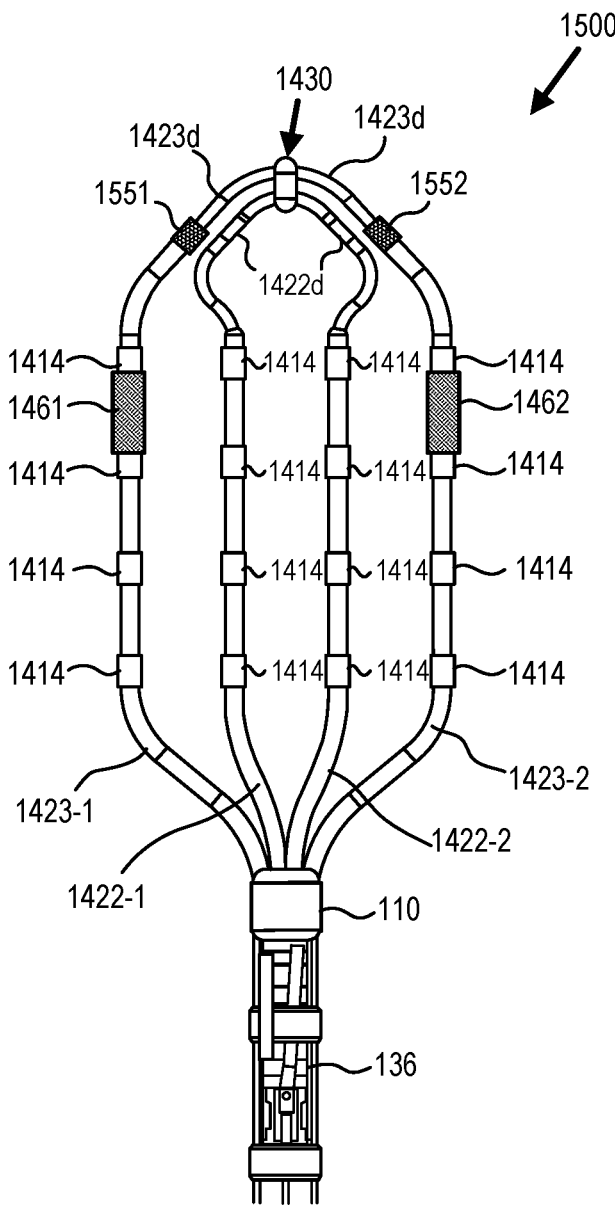
FIG. 15 illustrates a four-spline configuration of an electrode assembly, where distal electrodes are disposed at distal portions of outer splines, in accordance with embodiments of the present disclosure.

The present disclosure is not limited to distal electrodes on a distal coupler. In many embodiments, distal electrodes may be disposed at distal portions of the splines of the electrode assembly. FIG. 14 and FIG. 15 illustrate electrode assemblies 1400, 1500 with four splines, where distal electrodes are disposed on distal portions of splines. The electrode assembly 1400 and 1500 have similar configurations except for disposition of distal electrodes (e.g., 1451, 1452, 1551, 1552). For example, distal electrodes may be disposed on an inner spline assembly and/or an outer spline assembly of the electrode assembly. For example, in FIG. 14, the electrode assembly 1400 includes the distal electrodes 1451, 1542 disposed on the inner spline assembly 1422. In FIG. 15, the electrode assembly 1500 includes distal electrodes 1551, 1552 disposed on the outer spline assembly 1423. The distal electrodes can function in similar manner as discussed with respect to distal couplers 130, 1200, and 1300. For example, the distal electrodes can help with mapping, and therapeutic treatments (e.g., pacing, ablation, etc.). The distal electrodes can reach small spaces like the apex of a heart to map and/or deliver therapeutic treatments.

Referring to FIG. 14, the electrode assembly 1400 includes an inner spline assembly 1422 and an outer spline assembly 1423. The outer spline assembly 1423 surrounds the inner spline assembly 1422 on two sides. The inner spline assembly 1422 includes a first spline 1422-1, a second spline 1422-2, and a distal portion 1422*d* coupling the first spline 1422-1 and the second spline 1422-2. Similarly, the outer spline assembly 1423 includes a third spline 1423-1, a fourth spline 1423-2, and a distal portion 1423*d* coupling the third spline 1423-1 and the fourth spline 1423-2. As illustrated, the distal portions 1422*d* of the inner spline assembly 1422 is angled relative to each of the first spline 1422-1 and the second spline 1422-2. Similarly, the distal portion 1423*d* of the outer spline assembly 1423 is angled relative to each of the third spline 1423-1 and the fourth spline 1423-2. Furthermore, a set of spline electrodes 1414 (e.g., similar to electrodes 114 in FIG. 1) are distributed along the first spline 1422-1 and the second spline 1422-2 respectively, and another set of spline electrodes 1414 (e.g., similar to the electrodes 114 in FIG. 1) are distributed along the third spline 1423-1 and the fourth spline 1423-2. In the illustrated embodiment, 16 spline electrodes and 2 distal electrodes are represented. However, the present disclosure is not limited to a number of electrodes and more or less electrodes may be accommodated on the electrode assembly.

In the illustrated embodiment, the electrode assembly 1400 includes a distal coupler 1430 configured to couple the distal portions of the inner spline assembly 1422 and the outer spline assembly 1423. For example, the distal coupler 1430 includes holes spaced from each other, each hole receiving a distal portion of a spline assembly. The distal portion 1422d of the inner spline assembly 1422 is spaced from the distal portion 1423d of the outer spline assembly 1423 within the distal coupler 1430. In some embodiments, the distal coupler 1430 can have a similar construction as a distal portion (e.g., 302, 1202, 1302) of the distal couplers (e.g., 130, 1200, 1300) described herein.

In the illustrated embodiments, an electrode assembly (e.g., 1400, 1500) includes magnetic sensors 1461, 1462 configured for generating output indicative of a position of the electrode assembly 1400 with respect to a target area (e.g., within a heart). Based on the position information from the magnetic sensors 1461, 1462, proximity of electrodes (e.g., 112 or 132) to the target area can be determined. When the electrodes are at desired positioned with respect to the target area, electrical signals related to pacing are transmitted via the electrodes to the target area. In the illustrated embodiment, the magnetic sensors 1461, 1462 are disposed within the outer spline assembly 1423. For example, the magnetic sensors 1461, 1462 may be attached to the understructure of the outer spline assembly 1423 and covered with a spline cover.

Referring back to FIG. 11, a controller circuitry (e.g., the main electronic control unit 1112) can be communicatively coupled to the distal electrodes (e.g., 1451, 1452, 1551, 1552) and the magnetic sensors (e.g., 1461, 1462) of an electrode assembly (e.g., 1400, 1500). In some embodiments, the distal electrodes (e.g., 1451, 1452, 1551, 1552) transmit electrical signals to and from the controller circuitry (e.g., 1112) to perform pacing of a target tissue in response to position information from the magnetic sensors. For example, the controller circuitry (e.g., 1112) is configured to determine proximity of distal electrodes to the target tissues. When the distal electrodes at a specified position, the controller circuitry can generate pacing related signals so that the distal electrodes of the catheter can perform bipolar pacing of the target tissue during electrophysiology procedure.

In some embodiments, a display can be communicatively coupled to the controller circuitry (e.g., 1112 in FIG. 11). The controller circuitry (e.g., 1112 in FIG. 11) is further configured to generate and display a map indicative of positioning (e.g., a location and/or orientation with respect to a tissue) of the electrode assembly within a heart. The controller circuitry (e.g., 1112) determines position of the electrode assembly (e.g., 1400, 1500) within an apex portion of the heart based on the signals from the distal electrodes (e.g., 1451, 1452, 1551, 1552) only. In addition, signals may also be received from the spline electrodes (e.g., 1414) to further determine a position of the electrode assembly within the heart. For example, localization of electrode assembly within the heart can be based on an impedance localization system and/or hybrid magnetic and impedance tracking system such an EnSite™.

Figure 16:
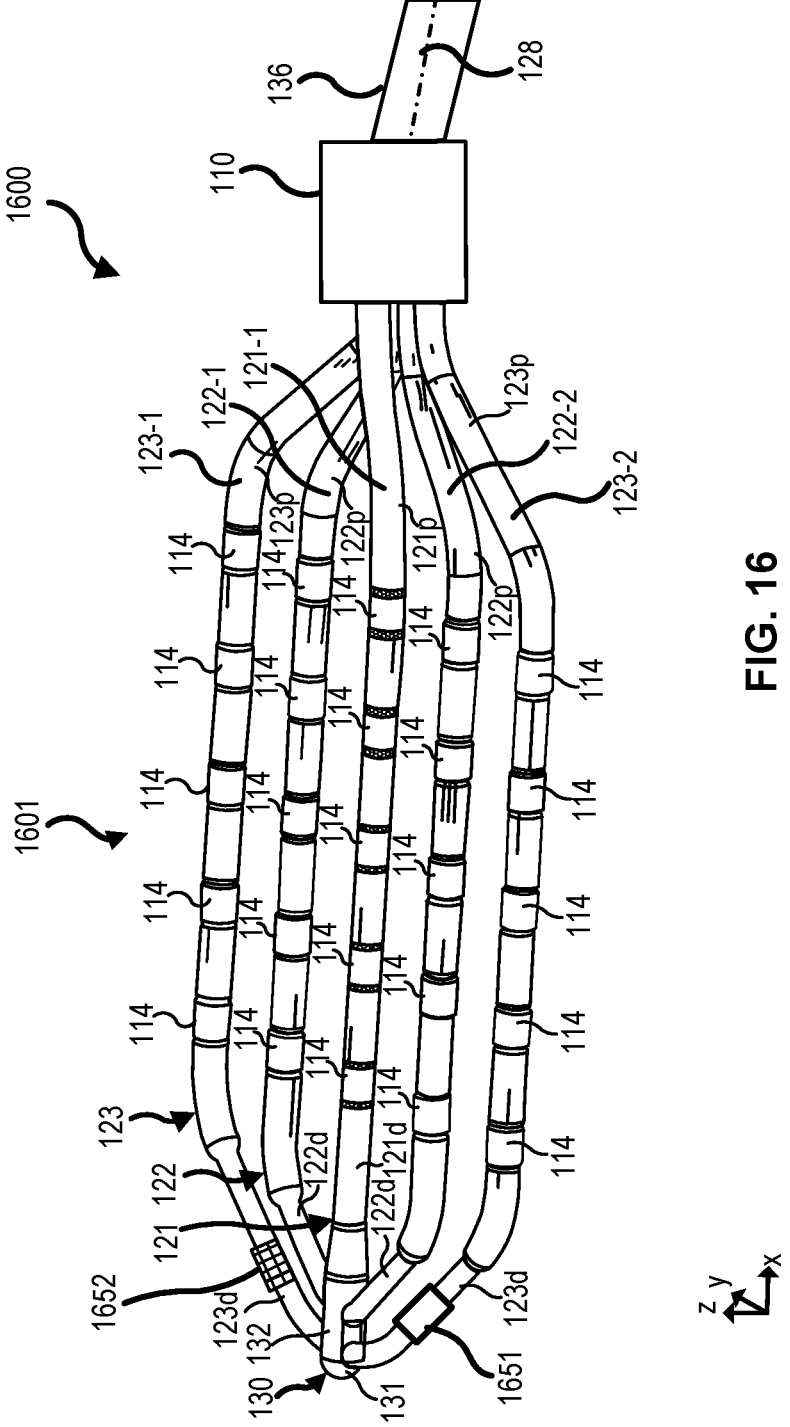
FIG. 16 illustrates a five-spline configuration of an electrode assembly, where distal electrodes are disposed at distal portions of outer splines and another distal electrode is disposed on a distal coupler assembly, in accordance with embodiments of the present disclosure.

FIG. 16 illustrate an electrode assembly 1601 with five splines 121, 122-1, 122-2, 123-1, and 123-2. The electrode assembly 1601 is substantially similar to the electrode assembly 101 (in FIG. 1), as indicated by same reference numbers. Details of similar features are discussed above and omitted here for brevity. In the illustrated embodiment, the electrode assembly 1601 includes distal electrodes 1651, 1652 disposed at distal portions of outer splines and another distal electrode 132 disposed on the distal coupler assembly 130. The distal electrodes 1651, 1652 can be structurally and functionally similar to the distal electrodes 1451 and 1452 or 1551 and 1552. The present disclosure is not limited to illustrated embodiments and other configurations are possible. For example, additional distal electrodes (e.g., similar to 1651, 1652) may be disposed on the distal portion 122d of the inner splines 122. One or more magnetic sensors (e.g., similar to 1461, 1462) may be disposed within the outer splines 123.

Example Embodiments

In one or more embodiments of the present disclosure, a catheter includes an elongated catheter shaft and an electrode assembly. The electrode assembly includes a first spline assembly, a second spline assembly, and a distal coupler assembly. The first spline assembly includes a distal portion and first spline electrodes distributed along the first spline assembly. The second spline assembly includes a distal portion and second spline electrodes distributed along the second spline assembly. The distal coupler assembly includes a base member and a distal electrode. The base member is configured to receive the distal portions of the first and second spline assemblies. The base member defines an opening configured to receive the distal portion of the second spline assembly. The distal electrode is configured to be mounted to the base member to secure the distal portion of the second spline assembly within the opening. Optionally, the distal electrode can be configured to transmit electrical signals via a wire. Optionally, the first spline assembly can be configured to route the wire to a proximal end of the first spline assembly. Optionally, the base member can include a proximal shaft portion and a distal shaft portion. The proximal shaft portion can be configured to receive and secure in place the distal portion of the first spline assembly. The distal shaft portion can include the opening to receive and secure in place the distal portion of the second spline assembly. Optionally, the opening can include a frame slot with a circumferential opening having an axially extending width and a transversely extending length, wherein a width of the circumferential opening is less than a maximum cross-sectional dimension of an understructure of the second spline assembly. Optionally, the frame slot can be configured to receive a minimum cross-section dimension of the distal portion of the second spline assembly and deliver the distal portion into the opening such that the distal portion can be rotated within the opening to secure the second spline assembly within the opening. In some optional embodiments, the distal portion of the second spline assembly can be rotated by approximately 90° within the opening such that the maximum cross-sectional dimension of the distal portion covers the frame slot to securely install the distal portion in the opening of the base member. In some optional embodiments, the opening is a cylindrical hole extending transversely along the distal shaft portion of the base member. Optionally, the distal shaft portion of the base member can include an electrode receiving portion configured to securely receive the distal electrode between a distal end and a proximal end of the distal shaft portion of the base member. Optionally, the base member and the distal electrode are one piece construction with an electrical wire directly connected to the distal electrode. Optionally, the electrode receiving portion of the distal shaft portion can include a shoulder at the distal end to prevent axial displacement of the distal electrode upon assembly. Optionally, the electrode receiving portion of the base member can include a chamfer at the proximal end to slidably receive a cover over the distal portion of the first spline assembly and abut against a proximal end of the distal electrode to secure and prevent axial displacement of the distal electrode on the distal shaft portion. Optionally, the base member can include a wire slot at a proximal end to facilitate receiving and coupling an electrical wire to the distal electrode via welding. Optionally, the base member can include a proximal shaft portion and a distal shaft portion, wherein the proximal shaft portion comprises a channel configured to receive the distal portion of the first spline assembly. Optionally, the first spline assembly can include an understructure with an enlarged distal end, and wherein the channel comprises an enlarged recess sized to receive the enlarged distal end of the first spline assembly and secure the first spline assembly to the proximal shaft portion of the base member. In some optional embodiments, the channel of the proximal shaft portion extends proximally and configured to route a wire from the distal electrode to a proximal end of the first spline assembly. In some optional embodiments, the channel of the proximal shaft portion has a depth to receive a sensor to be coupled to the first spline assembly. In some optional embodiments, the distal electrode is a hollow cylinder that includes axial slots extending from a distal end toward a proximal end. In some optional embodiments, each of the axial slots has a width and a length corresponding to the opening in the base member to facilitate slidably coupling of the distal electrode to the base member while the distal portion of the second spline assembly is secured in the opening. Optionally, the electrode assembly can be configured for ablation therapy, cardiac mapping, or pacing. Optionally, the distal electrode of the distal coupler assembly and a spline electrode of the first spline assembly or the second spline assembly can be configured for transmitting coordinated electrical signals to effect bipolar pacing. Optionally, the catheter can further include a third spline assembly that includes a distal portion and third spline assembly electrodes distributed along the third spline assembly. Optionally, the distal coupler assembly can further include a second opening configured to receive and secure the distal portion of the third spline assembly. Optionally, the opening of the base member can be spaced from the second opening of the base member and located distally from the second opening. Optionally, the first spline assembly can further include a first spline having the distal portion and a proximal portion. Optionally, the first spline electrodes can include a first set of electrodes distributed between the proximal portion and the distal portion of the first spline. Optionally, the second spline assembly can include a second spline having a distal portion and a proximal portion and a third spline having a distal portion and a proximal portion, wherein the distal portions of the second spline and the third spline are joined to form the distal portion of the second spline assembly. Optionally, the second spline electrodes can include a second set of electrodes distributed between the proximal portion and the distal portion of the second spline, and a third set of electrodes distributed between the proximal portion and the distal portion of the third spline. Optionally, the catheter can further include a third spline assembly that includes (a) a fourth spline having a distal portion and a proximal portion, (b) a fifth spline having a distal portion and a proximal portion, (c) a fourth set of electrodes distributed between the proximal portion and the distal portion of the fourth spline, and (d) a fifth set of electrodes distributed between the proximal portion and the distal portion of the fifth spline. Optionally, the second spline assembly can be disposed around the first spline assembly, the third spline assembly can be disposed around the second spline assembly, the second spline and the third spline can be disposed on either side of the first spline, and the fourth spline and the fifth spline can be disposed on either side of the first spline. Optionally, each of the first set of electrodes, the second set of electrodes, the third set of electrodes, the fourth set of electrodes, and the fifth set of electrodes can include at least 4 electrodes. Optionally, the catheter can further include a proximal connector; the first spline assembly can further include a proximal portion that is attached to and extends distally from the proximal connector, and the first spline electrodes can be distributed between the proximal portion and the distal portion of the first spline assembly. Optionally, the base member comprises an electrically conductive portion that is coated with an insulation material to electrically isolate the electrically conductive portion from the distal electrode of the distal coupler assembly. Optionally, the base member and the distal electrode can be configured for performing bipolar pacing of a target tissue.

In one or more embodiments of the present disclosure, a catheter includes an elongated catheter shaft and an electrode assembly. The electrode assembly includes a first spline assembly, a second spline assembly and a distal coupler. The first spline assembly includes a distal portion and first spline electrodes distributed along the first spline assembly. The second spline assembly includes a distal portion and second spline electrodes distributed along the second spline assembly. The distal coupler includes a first portion and a second portion made of electrically conductive materials and electrically isolated from each other. The second portion is configured to receive the distal portion of the first spline assembly. The first portion defines an opening configured to securely receive the distal portion of the second spline assembly within the opening. The distal coupler is configured as a single piece component. The first portion is configured to convey a first signal and the second portion is configured to receive a second signal. The first signal is isolated from the second signal. Optionally, the first portion of the distal coupler can be coated with an insulation material to electrically isolate the first portion from the second portion of the distal coupler. Optionally, the first portion and the second portion of the distal coupler can be configured for performing bipolar pacing of a target tissue. Optionally, the bipolar pacing of the target tissue can be performed during an electrophysiology procedure.

In one or more embodiments of the present disclosure, a catheter system includes an elongated catheter shaft, and electrode assembly, and controller circuitry. The electrode assembly includes a first spline assembly, a second spline assembly, a third spline assembly, and a distal coupler assembly. The first spline assembly includes a first distal portion and first spline assembly electrodes distributed along the first spline assembly. The second spline assembly includes a second distal portion and second spline assembly electrodes distributed along the second spline assembly. The third spline assembly includes a third distal portion and third spline assembly electrodes distributed along the third spline assembly. The distal coupler assembly includes a base member and a distal electrode. The base member is configured to couple the first spline assembly, the second spline assembly, and the third spline assembly. The base member defines a first opening and a second opening. The first opening is configured to receive and accommodate the second distal portion of the second spline assembly. The second opening is configured to receive and accommodate the third distal portion of the third spline assembly. The distal electrode is configured to be mounted to the base member to secure the second and third distal portions in the first opening and the second opening, respectively. The controller circuitry is communicatively coupled to the electrode assembly, the first spline assembly electrodes, the second spline assembly electrodes, and the distal electrode. The distal electrode sends electrical signals to the controller circuitry to determine a proximity of a distal end of the electrode assembly to a target tissue to facilitate accurate maneuvering of the electrode assembly around the target tissue. Optionally, the first spline assembly can be centrally disposed, the second spline assembly can be disposed on an outer side of the first spline assembly, and the third spline assembly can be disposed on an outer side of the second spline assembly. Optionally, each of the first and second openings can include a frame slot with a circumferential opening having an axially extending width and a transversely extending length, wherein the axially extending width can be less than a maximum cross-sectional dimension of an understructure of the second spline assembly, and wherein the axially extending width can be less than a maximum cross-sectional dimension of an understructure of the third spline assembly. Optionally, the catheter system can further include a display communicatively coupled to the controller circuitry, wherein the controller circuitry can be configured to generate and display a map indicative of positioning of the electrode assembly within a heart. Optionally, the catheter system can further include a display communicatively coupled to the controller circuitry, wherein the controller circuitry is configured to generate and display a map indicative of one or more electrical characteristics of tissue contacted by the distal electrode, the first spline assembly electrodes, the second spline assembly electrodes, and the third spline assembly electrodes. Optionally, the distal coupler assembly can be a two-piece component and the base member can be electrically isolated from the distal electrode. Optionally, the base member can be coated with an insulation material to electrically isolate the base member from the distal electrode. Optionally, the controller circuitry can be configured to generate signals for performing bipolar pacing to the target tissue based on signals transmitted by the base member and the distal electrode. Optionally, the controller circuitry can be configured to generate signals for perform bipolar pacing of the target tissue during an electrophysiology procedure.

In one or more embodiments of the present disclosure, a catheter includes an elongated catheter shaft and an electrode assembly coupled to the elongated shaft. The electrode assembly includes an inner spline assembly, an outer spline assembly, distal electrodes, magnetic sensors, and a distal coupler assembly. The inner spline assembly includes a first spline, a second spline, a distal portion coupling the first spline and the second spline, and inner spline assembly electrodes distributed along the first spline and the second spline. The outer spline assembly includes a third spline, a fourth spline, a distal portion coupling the third spline and the fourth spline, and outer spline assembly electrodes distributed along the third spline and the fourth spline. The distal electrodes are disposed along the distal portion of the inner spline assembly or the distal portion of the outer spline assembly. The magnetic sensors are configured for generating output indicative of a position and/or an orientation of the electrode assembly with respect to a target area. The distal coupler assembly is configured to receive the distal portions of the inner spline assembly and the outer spline assembly. Optionally, the distal electrodes can be disposed on the distal portion of the inner spline assembly. Optionally, each of the distal electrodes can be configured for transmitting electrical signals to effect pacing. Optionally, the electrical signals to effect pacing can be transmitted in response to the position and/or the orientation of the electrode assembly with respect to the target area. Optionally, the outer spline assembly can surround the inner spline assembly on two sides. Optionally, the distal portion of the inner spline assembly can be spaced from the distal portion of the outer spline assembly within the distal coupler assembly. Optionally, the distal portion of the inner spline assembly can be angled relative to each of the first spline and the second spline and the distal portion of the outer spline assembly can be angled relative to each of the third spline and the fourth spline. Optionally, the magnetic sensors can be disposed within the outer spline assembly. Optionally, the electrode assembly can further include a center spline assembly disposed between the first spline and the second spline of the inner spline assembly, the center spline assembly can include a center spline and center spline electrodes distributed along the center spline, the center spline can have a distal portion, and the distal coupler assembly can be coupled to the distal portion of the center spline. Optionally, the distal coupler assembly can further include a distal electrode disposed on the distal coupler assembly.

In one or more embodiments of the present disclosure, a catheter system includes an elongated catheter shaft, an electrode assembly, and controller circuitry. The electrode assembly includes an inner spline assembly, an outer spline assembly, distal electrodes, magnetic sensors, and a distal coupler assembly. The inner spline assembly includes a first spline, a second spline, a distal portion coupling the first spline and the second spline, and inner spline assembly electrodes distributed along the first spline and the second spline. The outer spline assembly includes a third spline, a fourth spline, a distal portion coupling the third spline and the fourth spline, and outer spline assembly electrodes distributed along the third spline and the fourth spline. The distal electrodes are disposed along the distal portion of the inner spline assembly or the distal portion of the outer spline assembly. The magnetic sensors are configured for generating output indicative of a position and/or an orientation of the electrode assembly with respect to a target area. The distal coupler assembly is configured to receive the distal portions of the inner spline assembly and the outer spline assembly. The controller circuitry is communicatively coupled to the inner spline assembly electrodes, the outer spline assembly electrodes, the distal electrodes, and the magnetic sensors. The distal electrode is configured for transmitting electrical signals to and from the controller circuitry to effect pacing of a target tissue in response to the position and/or the orientation of the electrode assembly with respect to the target area. Optionally, the catheter system can further include a display communicatively coupled to the controller circuitry, wherein the controller circuitry is further configured to generate and display a map indicative of positioning of the electrode assembly within a heart. Optionally, the controller circuitry can be configured to determine a position of the electrode assembly within an apex portion of the heart based on signals from the distal electrodes without receiving signals from the spline assembly electrodes. Optionally, the controller circuitry can be configured for effecting bipolar pacing of the target tissue during electrophysiology procedure. Optionally, the magnetic sensors can be disposed within the outer spline assembly.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A catheter comprising:
an elongated catheter shaft; and
an electrode assembly comprising:
a first spline assembly comprising a distal portion and first spline electrodes distributed along the first spline assembly;
a second spline assembly comprising a distal portion and second spline electrodes distributed along the second spline assembly; and
a distal coupler assembly comprising a base member configured to receive the distal portions of the first and second spline assemblies, and a distal electrode configured to extend along a longitudinal axis and over an outer circumference of the base member, wherein the base member defines an opening configured to receive the distal portion of the second spline assembly and the distal electrode is configured to be mounted to the base member to secure the distal portion of the second spline assembly within the opening.

2. The catheter of claim 1, wherein the distal electrode is configured to transmit electrical signals via a wire, and wherein the first spline assembly is configured to route the wire to a proximal end of the first spline assembly.

3. The catheter of claim 1, wherein the base member comprises:
a proximal shaft portion configured to receive and secure in place the distal portion of the first spline assembly; and
a distal shaft portion comprising the opening to receive and secure in place the distal portion of the second spline assembly.

4. The catheter of claim 3, wherein the opening comprises a frame slot with a circumferential opening having an axially extending width and a transversely extending length, wherein a width of the circumferential opening is less than a maximum cross-sectional dimension of an understructure of the second spline assembly.

5. The catheter of claim 4, wherein the frame slot is configured to receive a minimum cross-section dimension of the distal portion of the second spline assembly and deliver the distal portion into the opening such that the distal portion can be rotated within the opening to secure the second spline assembly within the opening.

6. The catheter of claim 5, wherein the distal portion of the second spline assembly is rotated by approximately 90° within the opening such that the maximum cross-sectional dimension of the distal portion covers the frame slot to securely install the distal portion in the opening of the base member.

7. The catheter of claim 3, wherein the opening is a cylindrical hole extending transversely along the distal shaft portion of the base member.

8. The catheter of claim 3, wherein the distal shaft portion of the base member comprises an electrode receiving portion configured to securely receive the distal electrode between a distal end and a proximal end of the distal shaft portion of the base member.

9. The catheter of claim 8, wherein the base member and the distal electrode are one piece construction with an electrical wire directly connected to the distal electrode.

10. The catheter of claim 8, wherein the electrode receiving portion of the distal shaft portion comprises a shoulder at the distal end to prevent axial displacement of the distal electrode upon assembly.

11. The catheter of claim 1, wherein the base member comprises a wire slot at a proximal end to facilitate receiving and coupling an electrical wire to the distal electrode via welding.

12. The catheter of claim 1, wherein the base member comprises a proximal shaft portion and a distal shaft portion, wherein the proximal shaft portion comprises a channel configured to receive the distal portion of the first spline assembly.

13. The catheter of claim 1, wherein:
the distal electrode is a hollow cylinder comprising axial slots extending from a distal end toward a proximal end; and
each of the axial slots has a width and a length corresponding to the opening in the base member to facilitate slidably coupling of the distal electrode to the base member while the distal portion of the second spline assembly is secured in the opening.

14. The catheter of claim 1, wherein the electrode assembly is configured for ablation therapy, cardiac mapping, or pacing.

15. The catheter of claim 1, further comprising:
a third spline assembly comprising a distal portion and third spline assembly electrodes distributed along the third spline assembly.

16. The catheter of claim 15, wherein:

the distal coupler assembly further comprises a second opening configured to receive and secure the distal portion of the third spline assembly; and the opening of the base member is spaced from the second opening of the base member and located distally from the second opening.

17. The catheter of claim 1, wherein:

the first spline assembly further comprises a first spline having the distal portion and a proximal portion, and the first spline electrodes comprise a first set of electrodes distributed between the proximal portion and the distal portion of the first spline.

18. The catheter of claim 17, wherein:

the second spline assembly comprises: a second spline having a distal portion and a proximal portion; and a third spline having a distal portion and a proximal portion, the distal portions of the second spline and the third spline joined to form the distal portion of the second spline assembly, and the second spline electrodes comprise: a second set of electrodes distributed between the proximal portion and the distal portion of the second spline, and a third set of electrodes distributed between the proximal portion and the distal portion of the third spline.

19. The catheter of claim 18, further comprises a third spline assembly comprising:

a fourth spline having a distal portion and a proximal portion;

a fifth spline having a distal portion and a proximal portion;

a fourth set of electrodes distributed between the proximal portion and the distal portion of the fourth spline; and a fifth set of electrodes distributed between the proximal portion and the distal portion of the fifth spline.

20. The catheter of claim 19, wherein the second spline assembly is disposed around the first spline assembly, and the third spline assembly is disposed around the second spline assembly, wherein the second spline and the third spline are disposed on either side of the first spline, and wherein the fourth spline and the fifth spline are disposed on either side of the first spline.

21. The catheter of claim 20, wherein each of the first set of electrodes, the second set of electrodes, the third set of electrodes, the fourth set of electrodes, and the fifth set of electrodes comprises at least 4 electrodes.

22. The catheter of claim 1, wherein the base member comprises an electrically conductive portion that is coated with an insulation material to electrically isolate the electrically conductive portion from the distal electrode of the distal coupler assembly.

23. The catheter of claim 22, wherein the base member and the distal electrode are configured for performing bipolar pacing to a target tissue.

24. A catheter comprising:

an elongated catheter shaft; and an electrode assembly comprising:

a first spline assembly comprising a distal portion and first spline electrodes distributed along the first spline assembly;

a second spline assembly comprising a distal portion and second spline electrodes distributed along the second spline assembly; and a distal coupler assembly comprising a base member configured to receive the distal portions of the first and second spline assemblies, and a distal electrode, wherein the base member defines an opening configured to receive the distal portion of the second spline assembly and the distal electrode is configured to be mounted to the base member to secure the distal portion of the second spline assembly within the opening, wherein the base member comprises:

a proximal shaft portion configured to receive and secure in place the distal portion of the first spline assembly; and a distal shaft portion comprising the opening to receive and secure in place the distal portion of the second spline assembly, wherein the opening comprises a frame slot with a circumferential opening having an axially extending width and a transversely extending length, and wherein a width of the circumferential opening is less than a maximum cross-sectional dimension of an understructure of the second spline assembly.

25. A catheter comprising:

an elongated catheter shaft; and an electrode assembly comprising:

a first spline assembly comprising a distal portion and first spline electrodes distributed along the first spline assembly;

a second spline assembly comprising a distal portion and second spline electrodes distributed along the second spline assembly; and a distal coupler assembly comprising a base member configured to receive the distal portions of the first and second spline assemblies, and a distal electrode, wherein the base member defines an opening configured to receive the distal portion of the second spline assembly and the distal electrode is configured to be mounted to the base member to secure the distal portion of the second spline assembly within the opening, and wherein the base member comprises an electrically conductive portion that is coated with an insulation material to electrically isolate the electrically conductive portion from the distal electrode of the distal coupler assembly.

* * * * *